United States Patent
Dube et al.

(10) Patent No.: US 12,357,627 B2
(45) Date of Patent: *Jul. 15, 2025

(54) PHARMACEUTICAL COMPOSITIONS OF CABOZANTINIB

(71) Applicant: AZURITY PHARMACEUTICALS, INC., Woburn, MA (US)

(72) Inventors: Sushant Omprakash Dube, Maharashtra (IN); Suprit Dilip Saoji, Maharashtra (IN); Pankaj Kisan Chatki, Telangana (IN); Sumitra Ashokkumar Pillai, Telangana (IN); Girish G. Kore, Maharashtra (IN)

(73) Assignee: AZURITY PHARMACEUTICALS, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/901,359

(22) Filed: Sep. 30, 2024

(65) Prior Publication Data
US 2025/0025456 A1   Jan. 23, 2025

Related U.S. Application Data

(63) Continuation of application No. 18/312,857, filed on May 5, 2023, now Pat. No. 12,138,255, which is a continuation of application No. 18/108,423, filed on Feb. 10, 2023, now Pat. No. 11,679,105, which is a continuation of application No. 17/673,583, filed on Feb. 16, 2022, now Pat. No. 11,590,122.

(30) Foreign Application Priority Data
Feb. 19, 2021   (IN) .............................. 202141007078

(51) Int. Cl.
   *A61K 31/47*   (2006.01)
   *A61K 9/10*   (2006.01)
(52) U.S. Cl.
   CPC ................ *A61K 31/47* (2013.01); *A61K 9/10* (2013.01)
(58) Field of Classification Search
   CPC ....................................................... A61K 31/47
   See application file for complete search history.

(56) References Cited

U.S. PATENT DOCUMENTS

| | | | |
|---|---|---|---|
| 8,877,776 B2 | 11/2014 | Brown et al. | |
| 11,590,122 B2 * | 2/2023 | Dube | A61K 9/2054 |
| 11,679,105 B1 * | 6/2023 | Dube | A61K 9/146 |
| | | | 514/312 |
| 2011/0020455 A1 | 1/2011 | Yoshida et al. | |
| 2012/0237593 A1 | 9/2012 | Comiskey et al. | |
| 2019/0275038 A1 | 9/2019 | Parlati et al. | |
| 2020/0190033 A1 | 6/2020 | Aftab et al. | |
| 2020/0261426 A1 * | 8/2020 | Park | A61K 31/366 |
| 2021/0206722 A1 | 7/2021 | Aftab et al. | |
| 2022/0280500 A1 | 9/2022 | Dube et al. | |
| 2022/0362235 A1 | 11/2022 | Dube et al. | |
| 2022/0387418 A1 | 12/2022 | Dube et al. | |

FOREIGN PATENT DOCUMENTS

| | | |
|---|---|---|
| WO | WO 2015/123639 A1 | 8/2015 |
| WO | WO 2018/064191 A1 | 4/2018 |
| WO | WO 2020/172120 A1 | 8/2020 |
| WO | WO 2021/152129 A1 | 8/2021 |

OTHER PUBLICATIONS

U.S. Appl. No. 18/312,857, filed May 5, 2023, Dube; Sushant Omprakash.*
U.S. Appl. No. 18/523,274, filed Nov. 29, 2023, Dube; Sushant Omprakash.*
CABOMETYX® (cabozantinib) tablets, for oral use Initial U.S. Approval: 2012 drug label, revised Jan. 2021.*
"CABOMETYX—cabozantinib tablet," Exelixis, Inc., 2021, 63 pages total.
Fumié Tanno, et al., Evaluation of hypromellose acetate succinate (HPMCAS) as a carrier in solid dispersions, Drug Dev Ind Pharm, 30(1):9-17 (Jan. 2004).
International Search Report and English translation of the Written Opinion of the International Searching Authority for International Application No. PCT/US22/16586, dated May 3, 2022.
Laberge et al., "Evaluation of the Effect of Food or Administration of a Proton Pump Inhibitor on the Single-Dose Plasma Pharmacokinetics of Cabozantinib in Healthy Adult Subjects," Celerion, Oct. 17, 2014, 1 page.
Lagace et al., "Developing a Discriminating Dissolution Procedure for a Dual Active Pharmaceutical Product with Unique Solubility Characteristics," Dissolution Technologies, Feb. 2004, pp. 13-17.
Nguyen et al., "Pharmacokinetics of cabozantinib tablet and capsule formulations in healthy adults," Anti-Cancer Drugs, 2016, vol. 27, No. 7, pp. 669-678.

* cited by examiner

*Primary Examiner* — Svetlana M Ivanova
(74) *Attorney, Agent, or Firm* — Birch, Stewart, Kolasch & Birch, LLP

(57) ABSTRACT

Pharmaceutical compositions are provided, which comprise cabozantinib or pharmaceutically acceptable salts thereof, and at least one pharmaceutically acceptable excipient, wherein the inventive compositions exhibit enhanced bioavailability compared to the currently marketed or commercially available formulations. The present invention also provides manufacturing processes thereof and use of the said inventive compositions for the prevention, treatment or prophylaxis of disorders in human patients in need thereof. The present invention relates to oral pharmaceutical compositions of cabozantinib, methods for their administration, processes for their production, and use of these compositions for treatment of diseases treatable by cabozantinib.

18 Claims, No Drawings

PHARMACEUTICAL COMPOSITIONS OF CABOZANTINIB

CROSS-REFERENCE TO RELATED APPLICATIONS

This application is a Continuation of application Ser. No. 18/312,857, filed on May 5, 2023, which is a continuation of application Ser. No. 18/108,423, filed on Feb. 10, 2023 (now U.S. Pat. No. 11,679,105, issued on Jun. 20, 2023) which is a continuation of application Ser. No. 17/673,583, filed on Feb. 16, 2022 (now U.S. Pat. No. 11,590,122, issued on Feb. 28, 2023), which claims foreign priority under 35 U.S.C. § 119(a) to Indian Application No. IN 202141007078, filed on Feb. 19, 2021, each of which are hereby expressly incorporated by reference into the present application.

FIELD OF THE INVENTION

The present invention relates to pharmaceutical compositions comprising cabozantinib or pharmaceutically acceptable salts thereof, and at least one pharmaceutically acceptable excipient, wherein the inventive compositions exhibit enhanced bioavailability compared to the currently marketed or commercially available formulations. Preferably, the invention provides a pharmaceutical composition comprising an amorphous solid dispersion, which comprises the cabozantinib or a pharmaceutically acceptable salt thereof, and at least one pharmaceutically acceptable carrier. The present invention also provides manufacturing processes thereof, and the use of the inventive compositions for prevention, treatment or prophylaxis of disorders in human patients in need thereof.

The present invention relates to oral pharmaceutical compositions of cabozantinib, methods for their administration, processes for their production, and use of these compositions for treatment of diseases treatable by cabozantinib.

BACKGROUND OF THE INVENTION

Cabozantinib (S)-malate is chemically described as N-(4-(6,7-dimethoxyquinolin-4-yloxy) phenyl)-N'-(4-fluorophenyl) cyclopropane-1,1-dicarboxamide, (2S)-hydroxybutanedioate and is a multiple receptor tyrosine kinase inhibitor. Examples of disorders that may be treated with cabozantinib include, but are not limited to renal cell carcinoma (RCC), hepatocellular carcinoma (HCC) and medullary thyroid cancer (MTC).

Cabozantinib is characterized as a Biopharmaceutical Classification System (BCS) class II compound, which means that it has low aqueous solubility and high permeability. Cabozantinib is practically insoluble in water (0.11 mg/mL in 0.01N HCl and practically insoluble at pH>4) and also exhibits polymorphism. Cabozantinib is poorly water soluble and hence, it has been difficult to formulate and deliver oral dosage forms which exhibit good bioavailability.

Cabozantinib is currently marketed under the brand names CABOMETYX® (EQ 20 mg base; EQ 40 mg base; EQ 60 mg base; National Drug Code Number 42388-023; NDA 208692) and COMETRIQ® (EQ 20 mg base; EQ 80 mg base; National Drug Code Number 42388-011; NDA 203756). CABOMETYX® is available in the form of film-coated tablets containing equivalent to 20 mg, 40 mg and 60 mg of cabozantinib. CABOMETYX® film-coated tablets contain inactive ingredients such as microcrystalline cellulose, lactose anhydrous, hydroxypropyl cellulose, croscarmellose sodium, colloidal silicon dioxide, and magnesium stearate, film coating contains hypromellose, titanium dioxide, triacetin, and iron oxide yellow.

CABOMETYX® is prescribed as 60 mg or 40 mg orally once daily for treatment of patients with advanced renal cell carcinoma (RCC) and for treatment of patients with hepatocellular carcinoma (HCC) who have been previously treated with sorafenib.

The package insert of CABOMETYX® discloses that the patients are instructed to take the tablet once daily at least 1 hour before or at least 2 hours after eating.

After oral administration of cabozantinib, high inter-subject variability for $C_{max}$ and AUC values was observed for both capsule and tablet formulations [CV % $C_{max}$: 51% for the tablet formulation, 61% for the capsule formulation; CV % $AUC_{0-last}$ or $AUC_{0-infinity}$: 40-43% for the tablet formulation, 43% for the capsule formulation]. The geometric mean $C_{max}$ of the tablet formulation was approximately 49% higher than the value observed for the capsule formulation. The geometric mean $AUC_{0-last}$ and $AUC_{0-infinity}$ values for the tablet formulation were also higher (15% and 19%, respectively) than those observed/or the capsule formulation.

The absolute bioavailability of cabozantinib has not been determined. Based on the mass balance study, however, at least 27% of the administered cabozantinib is renally excreted, and thus at least this fraction of the administered dose was absorbed. The need for administering such high doses of cabozantinib may be due to low bioavailability exhibited by CABOMETYX® and may be responsible for the adverse side effects associated with the use of cabozantinib such as hemorrhage, perforations and fistulas, thrombotic events, hypertension and hypertensive crisis, diarrhea, palmar-plantar erythrodysesthesia, and proteinuria. Moreover, low bioavailability results in more variable absorption and potential variability of the desired therapeutic response.

The drug absorption after oral administration generally depends on the release of the drug from the composition, the dissolution of the drug under physiological conditions, as well as its permeability across the gastrointestinal tract. A higher dissolution rate of a composition generally increases release of the drug from its composition, which is a prerequisite for adequate bioavailability of a drug. Because of this requirement, a good in vitro dissolution of the composition may lead to good and adequate in vivo plasma concentration, and therefore an adequate bioavailability.

Food also has a positive effect on oral absorption of weak base compounds such as cabozantinib, where bioavailability is enhanced through increased dissolution by stimulation and release of bile and pancreatic enzymes.

The bioavailability of cabozantinib is increased when given with a high-fat, high calorie meal relative to fasted conditions in healthy subjects administered a single oral dose of a cabozantinib formulation. The $C_{max}$ and AUC of cabozantinib increased by 41% and 57%, respectively, following a high-fat meal relative to fasted conditions in healthy subjects administered a single oral dose of cabozantinib formulation.

Commercially available preparations of cabozantinib pose risk of adverse effects, particularly if the patient ingests the tablets of cabozantinib with or after meals, particularly high fat meals, because the rate and extent of absorption ($C_{max}$ and AUC) are increased by 41% and 57%, respectively.

There exists a need to develop pharmaceutical compositions of cabozantinib which increases the bioavailability of cabozantinib, and which in turn reduces the dose of cabozantinib to be administered to a human subject. The dose which can be lower than the usual or the conventional dose, required to produce equal or higher therapeutic effect, may also reduce the side effects, thereby helping to limit the risk to the patient. There is an impending need for developing cabozantinib oral pharmaceutical compositions which exhibit improved bioavailability and results in reduced adverse events and provides enhanced patient safety.

There also exists a need to improve the bioavailability of cabozantinib in the fasted state and provide a composition which maintains optimal therapeutic concentrations of cabozantinib in the human subject and at the same time reduces the side effects exhibited by the same.

It is desirable to have a composition for oral administration which provides cabozantinib to a patient population with lower variability in bioavailability, thus providing consistent PK parameters (e.g., a narrower observed range for $C_{max}$ and AUC values) across a patient population to whom the composition is administered.

It is also desirable to have a composition for oral administration which provides enhanced bioavailability of cabozantinib in the fasted state compared to commercially available formulations, i.e., CABOMETYX®.

What is needed is a composition of cabozantinib that is suitable for oral administration to patients, and which provides more uniform plasma level(s) and sufficient cabozantinib exposure (AUC) in fasted state. What is also needed is an oral composition of cabozantinib, which when administered to a human subject, exhibits less variability in pharmacokinetic parameters (e.g., $C_{max}$, $AUC_{0-t}$ and $AUC_{0-infinity}$) than commercially available cabozantinib formulations (i.e., CABOMETYX®).

There exists a need for developing a stable pharmaceutical composition of cabozantinib suitable for oral administration, exhibiting improved solubility and increased bioavailability of cabozantinib when compared to the commercially available product (i.e., CABOMETYX®), wherein the composition remains stable for at least 6 months at 40° C./75% RH ("relative humidity") or 25° C./60% RH ("relative humidity").

There also exists a need for administering reduced daily doses of cabozantinib, wherein the inventive compositions exhibit enhanced bioavailability in fasted state and can be administered without regard to food.

It is very much desirable to have a pharmaceutical composition of cabozantinib for oral administration which provides enhanced bioavailability in the fasted state compared to commercially available product, e.g., CABOMETYX®. The increase in oral bioavailability will enable administration of cabozantinib at a significantly lower therapeutically effective doses than what are currently being used.

SUMMARY OF THE INVENTION

The present invention relates to pharmaceutical compositions comprising cabozantinib or its pharmaceutically acceptable salts thereof for oral administration, wherein said composition exhibits enhanced bioavailability in the fasted state, compared to the commercially available product (CABOMETYX®).

In an aspect, the invention provides a pharmaceutical composition comprising: an amorphous solid dispersion of cabozantinib, which comprises cabozantinib and at least one pharmaceutically acceptable carrier. The pharmaceutical composition may further comprises one or more pharmaceutical excipients.

In particular, the pharmaceutical composition is in a dosage form suitable for oral administration to a patient. The dosage form suitable for oral administration to a patient may preferably be selected from the group consisting of a tablet, a capsule, a caplet, beads, granules, a powder and an oral suspension. The dosage form suitable for oral administration to a patient may be a tablet comprising: (a) the amorphous solid dispersion of cabozantinib and (b) at least one pharmaceutically acceptable excipient. The tablet may comprise granules of the amorphous solid dispersion of cabozantinib, especially wherein the at least one pharmaceutical acceptable excipient comprises an intra-granular excipient(s) and/or an extra-granular excipient(s).

In an aspect, the dose of pharmaceutical composition comprising cabozantinib or a pharmaceutically acceptable salt thereof, is reduced by at least 10% in comparison to a commercially available product (CABOMETYX®).

In an aspect, the dose of pharmaceutical composition comprising cabozantinib or a pharmaceutically acceptable salt thereof, is reduced by at least 25% in comparison to a commercially available product (CABOMETYX®).

In another aspect, the dose of pharmaceutical composition comprising cabozantinib or a pharmaceutically acceptable salt thereof, is reduced by at least 50% in comparison to a commercially available product (CABOMETYX®).

In yet another aspect, the dose of pharmaceutical composition comprising cabozantinib or a pharmaceutically acceptable salt thereof, is reduced by at least 75% in comparison to a commercially available product (CABOMETYX®).

In an aspect, the pharmaceutical composition comprising cabozantinib or a pharmaceutically acceptable salt thereof exhibits less variability in at least one pharmacokinetic parameter (i.e., $C_{max}$, $AUC_{0-t}$ and $AUC_{0-infinity}$) compared to the commercially available product (i.e., CABOMETYX®), when administered orally to human subjects.

The present invention further relates to amorphous solid dispersions of cabozantinib. The present invention relates to stable pharmaceutical compositions for oral administration comprising amorphous solid dispersions of cabozantinib. The invention also relates to methods of administration to a patient in need thereof, particularly a human patient, in need of treatment of a disorder treatable with a multiple receptor tyrosine kinase inhibitor. Examples of disorders that may be treated with cabozantinib include, but are not limited to renal cell carcinoma (RCC), hepatocellular carcinoma (HCC) and medullary thyroid cancer (MTC).

The present invention also relates to methods for making amorphous solid dispersions of cabozantinib, methods for preparing pharmaceutical compositions thereof, and methods for treating disorders using the inventive pharmaceutical compositions.

In an aspect, the pharmaceutical composition suitable for oral administration to a human subject in need thereof, comprises amorphous solid dispersions of cabozantinib or a pharmaceutically acceptable salt thereof; wherein said composition exhibits enhanced bioavailability in the fasted state compared to the commercially available product (CABOMETYX®).

In another aspect, the pharmaceutical composition suitable for oral administration to a human subject in need thereof, comprises amorphous solid dispersions of cabozantinib or a pharmaceutically acceptable salt thereof, wherein the composition remains stable for at least 6 months at 40° C./75% RH ("relative humidity") or 25° C./60% RH ("relative humidity").

Each of embodiments described in this application may further have one or more of the following additional elements in any combination:

Element 1: the amorphous solid dispersions of cabozantinib may further comprise a pharmaceutically acceptable carrier.

Element 2: An amorphous solid dispersion comprising: (a) cabozantinib; and (b) at least one pharmaceutically acceptable carrier; wherein the dispersion is substantially free of cabozantinib crystals; and wherein moisture content of the dispersion is less than about 5.0% by weight.

Element 3: the amorphous solid dispersions of cabozantinib may be prepared by hot-melt extrusion, spray-drying or co-precipitation.

Element 4: the amorphous solid dispersions may have a weight ratio of the cabozantinib to the pharmaceutically acceptable carrier from about 1:1 to about 1:7. In certain aspects, the amorphous solid dispersion of cabozantinib or the pharmaceutical salt thereof has a weight ratio of cabozantinib to the pharmaceutically acceptable carrier from about 1:1 to about 1:7, preferably about 1:3 to about 1:6.

Element 5: the amorphous solid dispersions may comprise, consist essentially of or consist of a pharmaceutically acceptable carrier selected from hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), polyvinyl pyrrolidine (PVP), and mixtures thereof.

Element 6: the amorphous solid dispersions may further comprise one or more pharmaceutically acceptable excipients selected from the group consisting of pore-forming agents, diluents, binders, disintegrants, lubricants, glidants, surfactants, plasticizers, stabilizing agents, coating agents, antioxidants or combinations thereof.

Element 7: the inventive pharmaceutical compositions may comprise from about 2.5 mg to about 140 mg of cabozantinib.

Element 8: the inventive pharmaceutical compositions may preferably be in the form of a tablet, a capsule, a caplet, beads, granules, powder or oral suspension.

Element 9: the inventive pharmaceutical compositions may further comprise one or more pharmaceutically acceptable excipients selected from the group consisting of pore-forming agents, diluents, binders, disintegrants, lubricants, glidants, surfactants, plasticizers, stabilizing agents, coating agents, antioxidants or combinations thereof.

Element 10: the inventive pharmaceutical compositions may preferably be obtained by direct compression, wet granulation or dry granulation, e.g., a tablet dosage form obtained by direct compression, wet granulation or dry granulation.

Element 11: the inventive pharmaceutical compositions may preferably be in the form of a tablet comprising: (a) an amorphous solid dispersion of cabozantinib (b) at least one intra-granular excipient, (c) at least one extra-granular excipient, and (d) optionally, a coating.

Element 12: A pharmaceutical composition comprising: (a) cabozantinib; and (b) at least one pharmaceutically acceptable carrier; and (c) one or more pharmaceutically acceptable excipients; wherein the composition provides an in-vitro release of not less than about 70 wt % of the cabozantinib, within 30 minutes of dissolution in a 900 mL 0.01 N HCl dissolution medium, measured using USP Apparatus II, at 75 RPM and 37° C.

Element 13: the amorphous solid dispersions or the inventive pharmaceutical compositions preferably have a level of any unknown impurity that is less than about 1% (w/w), preferably less than about 0.8% (w/w), and more preferably less than about 0.5% (w/w) as measured by HPLC.

Element 14: a method for treating a proliferative disorder comprising administration of the pharmaceutical composition to a human subject in need thereof. For example, the amorphous solid dispersions or the inventive pharmaceutical compositions may preferably be used in a method for treating a proliferative disorder in a human subject, which method comprises: (a) providing a pharmaceutical composition; and (b) providing instructions for oral administration of the composition indicating that the composition can be administered to a human subject without regard to food.

Element 15: the composition exhibits enhanced bioavailability in the fasted state, compared to a commercially available product corresponding to the drug product corresponding to National Drug Code Number 42388-023 and NDA 208692 (CABOMETYX®). For example, the composition exhibits enhanced bioavailability in the fasted state, compared to a commercially available product having the same dosage amount.

Element 16: a dosage amount of the cabozantinib or the pharmaceutically acceptable salt thereof, is reduced by at least 10% in comparison to the commercially available product, preferably is reduced by at least 25% in comparison to the commercially available product, is reduced by at least 50% in comparison to the commercially available product, or is reduced by at least 75% in comparison to the commercially available product, wherein the commercially available product corresponds to the drug product corresponding to National Drug Code Number 42388-023 and NDA 208692 (CABOMETYX®). For example, because the composition according to the invention exhibits enhanced bioavailability in the fasted state, the dosage amount required may be less, compared to a commercially available product, and still achieve the same or substantially same desired therapeutic effect (e.g., the same AUC, $C_{max}$, $AUC_{0-t}$ and $AUC_{0-infinity}$).

Element 17: the composition exhibits less variability in at least one pharmacokinetic parameter, when orally administered to a human subject, compared to the commercially available product corresponding to the drug product corresponding to National Drug Code Number 42388-023 and NDA 208692 (CABOMETYX®), and wherein the pharmacokinetic parameter is selected from the group consisting of $C_{max}$, $AUC_{0-t}$ and $AUC_{0-infinity}$. For example, the composition exhibits less variability when orally administered, compared to a commercially available product having the same dosage amount.

Element 18: the "cabozantinib" refers to cabozantinib free base, a pharmaceutically acceptable salt, solvates or hydrates thereof, e.g., the "pharmaceutically acceptable salt" comprises cabozantinib salts, which are formed with inorganic or organic acids. The cabozantinib may preferably be cabozantinib (S)-malate.

Element 19: an amorphous solid dispersion comprising: (a) cabozantinib; and (b) at least one pharmaceutically acceptable carrier; wherein the dispersion is substantially free of cabozantinib crystals; and wherein moisture content of the dispersion is less than about 5.0% by weight.

Element 20: a pharmaceutical composition comprising: (a) cabozantinib; and (b) at least one pharmaceutically acceptable carrier; and (c) one or more pharmaceutically acceptable excipients; wherein the composition provides an in-vitro release of not less than about 70 wt % of the cabozantinib, within 30 minutes of dissolution in a 900 mL 0.01 N HCl dissolution medium, measured using USP Apparatus II, at 75 RPM and 37° C.

By way of non-limiting example, exemplary combinations applicable to the embodiments described in this application may include any combination with one or more of the elements described above.

DETAILED DESCRIPTION OF THE INVENTION

Unless defined otherwise, all the technical and scientific terms used herein have the same meanings as commonly known by a person skilled in the art. In the case that there is a plurality of definitions for the terms herein, the definitions provided herein will prevail.

Unless specified otherwise, all the percentages, portions and ratios in the present invention are on weight basis.

The terms "about" and "approximate," when used along with a numerical variable, generally means the value of the variable and all the values of the variable within a measurement or an experimental error (e.g., 95% confidence interval for the mean) or within a specified value (e.g., ±10%) within a broader range.

As used herein the term "cabozantinib" refers to cabozantinib free base or its pharmaceutically acceptable salts, solvates or hydrates thereof. In principle, any crystalline form or amorphous form of cabozantinib may be used for manufacturing the inventive pharmaceutical compositions of the present invention.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to cabozantinib salts which are formed with inorganic or organic acids.

By "solid dispersion" is meant a molecular dispersion of a compound, particularly a drug substance within a carrier. The term solid dispersion in general means a system in solid state comprising at least two components, wherein one component is dispersed substantially evenly throughout the other component(s). For example, solid dispersions may be the dispersion of one or more active ingredients in an inert carrier or matrix at solid state, prepared by the melting, solvent, or melting-solvent methods. While not wishing to be bound by theory, in a solid dispersion, the drug may be present in a molecular state, colloidal state, metastable state, or an amorphous state. Formation of a molecular dispersion may provide a means of reducing the particle size to nearly molecular levels (i.e., there are no particles).

The terms "pharmaceutical composition," "pharmaceutical product," "pharmaceutical dosage form," "dosage form," "composition", "formulation", etc., refer to a pharmaceutical composition administered to a patient in need of treatment, and is typically in the form of tablet, hard-gelatin capsule, soft-gelatin capsule, oral suspension, oral solution, enteric coated hard-gelatin capsule, enteric coated soft-gelatin capsule etc.

By "effective amount" or "therapeutically effective amount" is meant the amount of a drug sufficient to treat, prevent, or ameliorate a condition in a subject or patient. The effective amount of cabozantinib or pharmaceutically acceptable salt thereof, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

The terms "carrier" and "pharmaceutically acceptable carrier" are interchangeable. The carrier is able to form a matrix embedding (surrounding) the active ingredient. The matrix may comprise one carrier or a mixture of two or more carriers. The carrier used in the solid dispersion of the present invention may be an enteric polymer or non-enteric polymer.

The term "solubility" means solubility of cabozantinib or its pharmaceutically acceptable salts in media such as water, buffer, gastrointestinal simulated fluid, gastrointestinal fluid and the like.

The term "in vivo" in general means in the living body of a plant or animal, whereas the term "in vitro" generally means outside the body and in an artificial environment.

The term "reduced dose" as used herein refers to a therapeutically effective dose of cabozantinib, which is less than the usual or conventional dose required to produce equal or higher therapeutic effect.

The term "subject" refers to an animal, including a human or non-human. The terms patient and subject may be used interchangeably herein.

"Bioequivalence" refers to the absence of a significant difference between the bioavailability, i.e., the mean ratio of AUC (over 24 hours) and the mean ratio of $C_{max}$ is within 80% to 125% between two pharmaceutical drug products (e.g., a test composition and a reference composition) over the course of a period of time, at the same dose and under the same conditions. The determination of whether or not a test composition is bioequivalent to a reference composition is determined by performing a study, referred to as a bioequivalence or comparative bioavailability study, in a group of subjects under controlled conditions.

The term "bioavailability" indicates the extent to which a drug or another substance is utilized by a target tissue after administration. For example, "bioavailability" may refer to the fraction of drug absorbed following administration to a subject or patient under fed or fasted state.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0\text{-}infinity}$" means the area under a plasma drug concentration-time curve from time point of 0 to infinity after drug administration.

The term "$AUC_{0\text{-}t}$" means the area under a plasma drug concentration-time curve from time point of 0 to t after drug administration, "t" is time in hours ranges from 24-72 hours. For instance, term "$AUC_{0\text{-}24}$" means the area under a plasma drug concentration-time curve from time point of 0 to 24 hours after drug administration.

As used herein, the term "enhanced bioavailability" refers to increase in concentration of the active ingredient in the body fluid provided by the compositions of the present invention when compared to concentration of the active ingredient in the body fluid obtained from a reference (such as CABOMETYX®) under identical conditions. In certain aspects, the bioavailability (e.g., AUC, $C_{max}$ and/or $T_{max}$) of cabozantinib when formulated as described herein is enhanced at least about 15%, but may be greater than 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 325%, 350%, 375% &

400% of the dose administered when compared to CABOMETYX® under identical conditions.

Pharmacokinetic parameters for the compositions can be measured in a single or multiple dose study using a replicate or a non-replicate design. For example, the pharmacokinetic parameters can be measured in a single dose pharmacokinetic study using a two-period, two-sequence crossover design. Alternately, a four-period, replicate design crossover study may also be used. Pharmacokinetic parameters characterizing rate and extent of cabozantinib absorption are evaluated statistically. The area under the plasma concentration-time curve from time zero to the time of measurement of the last quantifiable concentration ($AUC_{0-t}$) and to infinity ($AUC_{0-infinity}$), $C_{max}$, and $T_{max}$ can be determined according to standard techniques. Statistical analysis of pharmacokinetic data is performed on logarithmic transformed data (e.g., $AUC_{0-t}$, $AUC_{0-infinity}$, or $C_{max}$ data) using analysis of variance (ANOVA).

Reference throughout this specification will be made to the administration of a pharmaceutical composition under fed conditions or fasted conditions. It is well understood in the art that the pharmacokinetic performance of some compositions is affected by the presence or absence of food in the gastrointestinal system. These references thus relate to the normally accepted administration circumstances that are referred to in the art as "fed" or "fasted."

As used herein, the term "fasted state" means that the human or other mammal has not ingested 500 calories or more than 500 calories for at least one hour before taking cabozantinib solid oral dosage form and for at least two hours after taking cabozantinib solid oral dosage form.

As used herein, the term "fed state" refers to a human who has eaten a United States Food and Drug Administration (FDA) standard high fat breakfast (or other meal containing a comparable quantity of fat and calories) within said time period. The meal is high in both fat (approximately 50% of total calorie content of the meal) and calories (approximately 800-1000 calories).

The term "food effect" as used herein means food-drug interactions which either decrease or increase the extent of drug absorption. In other words, the bioavailability for a drug is altered when administered under fasted state, in comparison to the drug when administered in the fed state. It may refer to a relative difference in one or more of $AUC_{0-infinity}$, $AUC_{0-t}$ and/or $C_{max}$ of a drug, when said drug or a formulation thereof is administered orally to a human, concomitantly with food or in a fed state as compared to the same values when the same formulation is administered in a fasted state or without food.

In certain aspects, the food effect may be defined as the ratio of the $C_{max}$ and/or AUC values of the tested drug in fed versus fasted states. Measuring the $C_{max}$ and/or AUC values of the tested drug in fed and in fasted states is standard practice in the art. Reduction of food effect can be determined by comparing the value of the ratio from the composition or pharmaceutical composition of the invention and the value of a composition without the solubilized form disclosed in the present invention.

In certain embodiments, the pharmaceutical compositions described herein reduce or eliminate the food effect. As used herein, "reducing the food effect" refers to narrowing the difference in bioavailability, e.g., $AUC_{0-infinity}$, $AUC_{0-t}$ and/or $C_{max}$ for a drug administered under fasted states in comparison to the drug administered under fed states. In certain aspects, the food effect is eliminated. Thus, upon oral administration of a pharmaceutical composition as described herein, to a mammal in need thereof, there is not a significant food effect. In other words, the difference between a pharmacokinetic parameter measured after oral administration to a mammal with and without food, respectively, is less than 40%, e.g., less than 35%, less than 30%, less than 25%, less than 20%, less than 15%, less than 10 or less than 5%. Preferably the composition or the pharmaceutical composition of the invention has at least 15% reduced food effect, preferably 20%, preferably 25%, preferably 30%, preferably 40%, reduced food effect.

The difference in AUC of the compositions of the present invention, when administered in the fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $C_{max}$ of the compositions of the present invention, when administered in fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In some embodiments, administration of the pharmaceutical composition to fed and fasted subjects produce a coefficient of variation in $AUC_{0-t}$, $T_{max}$, $C_{max}$ and/or $AUC_{0-infinity}$ of less than about 60% (e.g., less than 55%, 50%, 45%, 40%, 35%, 30%, 25%, 20%, and 15%). In particular embodiments, the coefficient of variation in $AUC_{0-t}$, $T_{max}$, $C_{max}$ and/or $AUC_{0-infinity}$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

Oral administration of the inventive pharmaceutical compositions enhances the bioavailability of the cabozantinib making it possible to use reduced doses of cabozantinib (e.g., 2.5, 5, 10, 15, 20, 30, 35, 40, 45 and 50 mg per day) while achieving same or substantially similar therapeutic efficacy as compared to the commercially approved doses (e.g., 20, 40, and 60 mg per day). On the other hand, the inventive pharmaceutical composition allows administration of a lower dose while retaining the therapeutic efficacy of cabozantinib (e.g., 2.5, 5, 10, 15, 20, 30, 35, 40, 45 and 50 mg per day), resulting in reduced undesirable side effects such as hemorrhage, perforations and fistulas, thrombotic events, hypertension and hypertensive crisis, diarrhea, palmar-plantar erythrodysesthesia, proteinuria, associated with the use of conventional doses.

In certain embodiments, following administration of the pharmaceutical composition to subjects (e.g., fed or fasted condition), the mean bioavailability is greater than about 20% (e.g., greater than 25%, 30%, 35%, 40%, 45%, 50%, 55%, 60%, 65%, 70%, 75%, 80%, 85%, 90%, 95%, or even 99%) or between about 20% to about 90% (e.g., from 20% to 30%, from 20% to 40%, from 20% to 50%, from 20% to 60%, from 20% to 70%, from 20% to 80%, from 20% to 90%, from 30% to 40%, from 30% to 50%, from 30% to 60%, from 30% to 70%, from 30% to 80%, from 30% to 90%, from 40% to 50%, from 40% to 60%, from 40% to 70%, from 40% to 80%, from 40% to 90%, from 50% to 60%, from 50% to 70%, from 50% to 80%, from 50% to 90%, from 60% to 70%, from 60% to 80%, from 60% to 90%, from 70% to 80%, from 70% to 90%, and from 80% to 90%).

According to the embodiments of the invention, the amorphous solid dispersion comprises cabozantinib and at least one pharmaceutically acceptable carrier selected from one or more of hydroxypropyl methyl cellulose acetate succinate (HPMC-AS), polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), and polyvinyl pyrrolidine (PVP).

According to the embodiments of the invention, the hydroxypropyl methylcellulose acetate succinate (HPMC-AS) comprises various types, such as LF, LG, MF, MG, HF, LMP, MMP and HG, etc., the first letters L, M and H of the type's names mean the pH level at the beginning of dissolution of HPMC-AS. For example, L refers to low level (e.g., HPMC-AS begins to be dissolved when the pH value is more than 5.5), M refers to middle level (e.g., HPMC-AS begins to be dissolved when the pH value is more than 6.0), H refers to high level (e.g., HPMC-AS begins to be dissolved when the pH value is more than 6.5). The second letters F and G refer to the particle size of HPMC-AS, where F refers to fine powder, and G refers to granular. In some embodiments, the type of HPMC-AS is LF; in some embodiments, the type of HPMC-AS is MF; in some embodiments, the type of HPMC-AS is HG.

Certain embodiments herein relate to inventive pharmaceutical compositions which are stable, e.g., stable over the shelf life of the drug product. As used herein, the term "stable" is defined as no more than about 5% loss of cabozantinib under typical commercial storage conditions. In certain embodiments, the compositions of the present invention will have no more than about 3% loss of cabozantinib, more preferably, no more than about 2% loss of cabozantinib, under typical commercial storage conditions. The composition retains at least about 95% of the potency of cabozantinib after storing the composition at 40° C. and 75% relative humidity for at least three months. In certain aspects, the term "stable" refers to chemical stability, wherein not more than 2% w/w of total related substances are formed on storage at accelerated conditions of stability at 40° C. and 75% relative humidity or at 25° C. and 60% relative humidity for a period of at least three months or to the extent necessary for use of the composition.

An embodiment relates to a pharmaceutical composition comprising an effective amount of amorphous solid dispersion of cabozantinib, wherein the level of any unknown impurity is less than about 1% (w/w), preferably less than about 0.8% (w/w), preferably less than about 0.5% (w/w) as measured by HPLC.

In particular, the Hydroxy impurity (i.e., N-(4-fluorophenyl)-N-(4-hydroxyphenyl) cyclopropane-1,1-dicarboxamide) may be monitored. The structure of Hydroxy impurity is shown below:

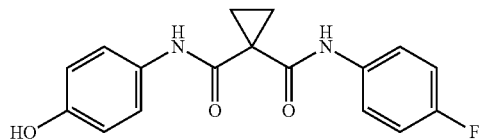 [SMILES: O=C(Nc1ccc(O)cc1)C1(C(=O)Nc2ccc(F)cc2)CC1]

An embodiment relates to a pharmaceutical composition comprising an effective amount of amorphous solid dispersion of cabozantinib, wherein the level of any Hydroxy impurity is less than about 0.5% (w/w), preferably less than about 0.2% (w/w) as measured by HPLC.

Pharmaceutically Acceptable Salts of Cabozantinib

Pharmaceutically acceptable salts of cabozantinib may be formed as acid addition salts, for example with organic or inorganic acids.

Suitable inorganic acids include, but are not limited to, halogen acids, such as hydrochloric acid, sulfuric acid, or phosphoric acid.

Suitable organic acids include, but are not limited to, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, malic acid, tartaric acid, citric acid, amino acids, such as glutamic acid or aspartic acid, maleic acid, benzoic acid, salicylic acid, cinnamic acid, or other organic protonic acids, such as ascorbic acid. Useful salt of cabozantinib for preparing inventive compositions herein is cabozantinib (S)-malate.

Dosage and Administration

The dose of the therapeutic compound will be in the range from about 2.5 to about 50 mg per day. Exemplary unit doses of therapeutic compound range from 2.5 mg to 50 mg, including unit dosages of 2.5 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg and 140 mg. Cabozantinib or its pharmaceutically acceptable salt thereof may be present in amounts totaling 1-95% by weight of the total weight of the composition.

The effective dosage range of the pharmaceutically acceptable salts may be calculated based on the weight of the active moiety to be delivered. If the salt exhibits activity itself, the effective dosage may be estimated as above using the weight of the salt, or by other means known to those skilled in the art.

Solid Dispersions of Cabozantinib

The term "solid dispersion" refers to a system in a solid-state comprising at least two components, wherein one component is dispersed throughout the other component or components.

The solid dispersions of cabozantinib may be formed by any conventional technique, e.g., spray drying, co-grinding, hot melt extrusion, freeze drying, rotary evaporation, solvent evaporation, co-precipitation, lyophilization, or any suitable solvent removal process. In an embodiment, solid dispersions of cabozantinib of the present application comprises amorphous forms of cabozantinib free base or a pharmaceutically acceptable salt thereof, and a pharmaceutically acceptable carrier.

In an embodiment, the present invention provides amorphous solid dispersion comprising (i) cabozantinib, (ii) at least one pharmaceutically acceptable carrier, and (iii) one or more pharmaceutically acceptable excipients selected from group comprising of pore-forming agents, diluents, binders, disintegrants, lubricants, glidants, surfactants, plasticizers, stabilizing agents, coating agents, antioxidants or combinations thereof.

In an embodiment, amorphous solid dispersion of cabozantinib or its pharmaceutically acceptable salt thereof, further comprises a pharmaceutically acceptable carrier and at least one pore-forming agent.

In another embodiment, amorphous solid dispersion of cabozantinib or its pharmaceutically acceptable salt thereof, further comprises a pharmaceutically acceptable carrier and optionally at least one plasticizer or an antioxidant.

In another embodiment, amorphous solid dispersion of cabozantinib or its pharmaceutically acceptable salt thereof, wherein the solid dispersion further comprises a pharmaceutically acceptable carrier and at least one plasticizer or an antioxidant, wherein the pharmaceutically acceptable carrier may be an enteric or a non-enteric polymer.

In certain embodiments, a pharmaceutically acceptable carrier used in the solid dispersion may be an enteric or a non-enteric polymer.

In certain embodiments, the enteric polymers are selected from the group consisting of cellulose acetate phthalate, cellulose acetate trimellitate, cellulose acetate succinate, methyl cellulose phthalate, ethylhydroxymethylcellulose phthalate, hydroxypropylmethylcellulose phthalate (HPMCP), hydroxypropylmethyl cellulose acetate succinate (HPMC-AS), hydroxypropylmethyl cellulose acetate maleate, hydroxypropylmethylcellulose trimellitate, carboxymethylethyl cellulose, polyvinyl butyrate phthalate, polyvinyl acetate phthalate, a methacrylic acid/ethyl acrylate copolymer and a methacrylic acid/methyl methacrylate copolymer, preferably selected from the group consisting of HPMCP, HPMC-AS, hydroxypropylmethyl cellulose acetate maleate and hydroxypropylmethylcellulose trimellitate, and more preferably is HPMC-AS.

In certain embodiments, the non-enteric polymers are selected from the group consisting of hydroxypropyl methylcellulose, hydroxypropyl cellulose, hydroxyethyl cellulose, polyvinylpyrrolidone (povidone), poly(vinylpyrrolidone/vinylacetate) (copovidone; For example: Plasdone® S630 Ultra), polyvinylcaprolactam/polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyvinyl alcohol, partially saponified polyvinylalcohol, macrogolglycerol hydroxystearate, and maltodextrins.

In some embodiments, the amorphous solid dispersion of cabozantinib or its pharmaceutically acceptable salt thereof, comprises a pharmaceutically acceptable carrier, where the weight ratio of the cabozantinib to the pharmaceutically acceptable carrier is from about 1:6 to about 1:1 (e.g., from 1:6 to 1:2, from 1:6 to 1:2.5, from 1:6 to 1:3, from 1:6 to 1:3.5, from 1:6 to 1:4, from 1:6 to 1:4.5, from 1:6 to 1:5, from 1:5 to 1:2, from 1:5 to 1:2.5, from 1:5 to 1:3, from 1:5 to 1:3.5, from 1:5 to 1:4, from 1:5 to 1:4.5, from 1:5 to 1:1.5, from 1:4 to 1:1.5, from 1:4 to 1:2, from 1:4 to 1:2.5, from 1:4 to 1:3, from 1:4 to 1:3.5, from 1:3 to 1:1.5, from 1:3 to 1:2, from 1:3 to 1:2.5, and from 1:2 to 1:1.5).

Solid dispersions of the present invention optionally may further include one or more organic acids. The organic acid may be selected from acetic acid, propionic acid, octanoic acid, decanoic acid, dodecanoic acid, glycolic acid, lactic acid, fumaric acid, succinic acid, adipic acid, pimelic acid, malic acid, tartaric acid, citric acid, glutamic acid, aspartic acid, maleic acid, benzoic acid, salicylic acid, phthalic acid, phenylacetic acid, cinnamic acid and ascorbic acid. The concentration of organic acid in the inventive compositions may range from about 1 mg to about 100 mg.

The amorphous solid dispersions of the present invention optionally may include one or more surfactants. Surfactants are compounds which are capable of improving the wetting of the drug and/or enhancing the dissolution. The surfactants can be selected from hydrophilic surfactants or lipophilic surfactants or mixtures thereof. The surfactants can be anionic, nonionic, cationic, and zwitterionic surfactants. Surfactants according to the present invention include, but not limited to, polyoxyethylene alkylaryl ethers such as polyoxyethylene lauryl ether, polyoxyethylene cetyl ether, polyoxyethylene stearyl ether; polyethylene glycol fatty acid esters such as PEG monolaurate, PEG dilaurate, PEG distearate, PEG dioleate; polyoxyethylene sorbitan fatty acid ester such as polysorbate 40, polysorbate 60, polysorbate 80; sorbitan fatty acid mono esters such as sorbitan monolaurate, sorbitan monooleate, sorbitan sesquioleate, sorbitan trioleate, sodium lauryl sulfate, sodium dioctyl sulfosuccinate (DOSS), lecithin, stearylic alcohol, cetostearylic alcohol, cholesterol, polyoxyethylene ricin oil, polyoxyethylene fatty acid glycerides, Kolliphor® RH 40, and the like or combinations thereof. The concentration of surfactant ranges from about 1% to about 10% w/w of carrier concentration.

Amorphous solid dispersions of the present invention may further include antioxidants selected from group consisting of α-tocopherol, β-carotene, butylated hydroxytoluene (BHT), butylated hydroxyanisole (BHA), tartaric acid, tert-butythydroquinone (TBHQ), propyl gallate (PG).

Amorphous solid dispersions of the present invention may further include plasticizers selected from group consisting of polyethylene glycol (such as PEG-8000, PEG-3350), propylene glycol, polyethylene oxide, 1,2-butylene glycol, 2,3-butylene glycol, styrene glycol, diethylene glycol, triethylene glycol, tetraethylene glycol and monoisopropyl ether, propylene glycol monoethyl ether, ethylene glycol monoethyl ether, diethylene glycol monoethyl ether, sorbitol lactate, ethyl lactate, butyl lactate, ethyl glycolate, triethyl citrate, acetyl triethyl citrate, tributyl citrate, tartaric acid, poloxamer (such as Pluronic® 407, Pluronic® 188), triacetin, stearic acid, Gleceryl behenate and allyl glycolate. The concentration of plasticizer ranges from about 0.5% to about 20% w/w of total composition.

In some embodiments herein, the percentage loading of cabozantinib in solid dispersion is from about 1% to about 90% (w/w) (e.g., from 1% to 19%, from 10% to 19%, from 10% to 20%, from 10% to 30%, from 10% to 40%, from 10% to 50%, from 10% to 60%, from 10% to 70%, from 10% to 80%, from 10% to 90%, from 20% to 30%, from 20% to 40%, from 20% to 50%, from 20% to 60%, from 20% to 70%, from 20% to 80%, from 20% to 90%, from 21% to 30%, from 21% to 34%, from 21% to 40%, from 21% to 50%, from 21% to 60%, from 21% to 70%, from 21% to 80%, from 21% to 90%, from 30% to 40%, from 30% to 50%, from 30% to 60%, from 30% to 70%, from 30% to 80%, from 30% to 90%, from 36% to 40%, from 36% to 49%, from 36% to 60%, from 36% to 70%, from 36% to 80%, from 36% to 90%, from 40% to 50%, from 40% to 60%, from 40% to 70%, from 40% to 80%, from 40% to 90%, from 50% to 60%, from 50% to 70%, from 50% to 80%, from 50% to 90%, 51% to 60%, from 51% to 70%, from 51% to 80%, from 51% to 90%, from 60% to 70%, from 60% to 80%, from 60% to 90%, from 70% to 80%, and from 70% to 90%). In some preferred embodiments, the percentage loading of cabozantinib is from about 10% to about 60% (w/w) (e.g., from 10% to 20%, from 10% to 30%, from 10% to 40%, from 10% to 50%, from 10% to 60%, from 20% to 30%, from 20% to 40%, from 20% to 50%, from 20% to 60%, from 30% to 40%, from 30% to 50%, from 30% to 60%, from 40% to 50%, and from 40% to 60%).

In an embodiment, amorphous solid dispersions of cabozantinib or its pharmaceutically acceptable salts are obtained by hot melt extrusion. The term hot-melt extrusion or hot-melt extruded is used herein to describe a process whereby a composition is heated and/or compressed to a molten (or softened) state and subsequently forced through an orifice in a die where the extruded product is formed into its final shape in which it solidifies upon cooling. The blend is conveyed through one or more heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and disaggregated. The die can be a dual manifold, multi-manifold or feed-block style die.

The hot-melt extrusion used for the preparation of the pharmaceutical composition of the present invention has to be conducted at temperatures below 150° C. Preferably, the hot-melt extrusion is conducted at a temperature of 30-150° C., more preferred at a temperature of 100-150° C. The hot-melt extrusion has to be carried out at a temperature that allows the dissolution of the cabozantinib or its pharmaceutically acceptable salts used as staring material within the mixture of enteric polymer and optionally at least one plasticizer or an antioxidant.

In an embodiment, amorphous solid dispersions of cabozantinib or its pharmaceutically acceptable salts are obtained by spray drying process. Spray dried dispersions are obtained by dissolving drug and the carrier in an organic solvent and then spray-drying the solution. The formulation and process conditions are chosen so that the solvent quickly evaporates from the droplets, allowing insufficient time for phase separation or crystallization.

In an embodiment, cabozantinib, at least one enteric polymer and at least one organic acid are mixed with one or more of organic solvents. Suitable solvents for mixing are selected from methanol, ethanol, isopropanol (IPA), ethyl acetate, dichloromethane (DCM), ethylene chloride, chloroform, acetonitrile, acetone and mixtures thereof.

The resultant amorphous solid dispersions of cabozantinib can be blended with one or more excipients, as described herein, and then granulated and/or compacted to produce a final blend for encapsulating or tableting.

In particular embodiments, the amorphous solid dispersion of cabozantinib may be combined with one or more excipient(s), e.g., such as a binding agent, a filler, a disintegrating agent, a wetting agent, a glidant, and a lubricant.

Cabozantinib used in the process for preparing the solid dispersion may be in crystalline or amorphous form. Alternatively, it may be obtained in situ from a previous processing step. The cabozantinib in the obtained solid dispersion may be present in either crystalline or amorphous form.

A solid that is in the "amorphous" solid state form means that it is in a non-crystalline state. Amorphous solids generally possess crystal-like short-range molecular arrangement, but no long-range order of molecular packing as are found in crystalline solids. The solid-state form of a solid, such as the drug substance in the amorphous dispersion, may be determined by Polarized Light Microscopy, X-Ray Powder Diffraction (XPRD), Differential Scanning Calorimetry (DSC), or other standard techniques known to those of skill in the art.

Pure amorphous form of cabozantinib is highly hygroscopic in nature and has a tendency to absorb moisture when stored at 25° C. and 60% RH. It has been seen that pure amorphous form of cabozantinib converts to crystalline form after absorbing about 5% moisture. The inventors of the present application have surprisingly found that a composition comprising amorphous solid dispersion of cabozantinib, at least one carrier, contains moisture less than about 5% when stored at 25° C./60% RH for at least 3 months, and substantially free from crystalline cabozantinib. Amorphous cabozantinib, compared to its crystalline forms, is less moisture stable. On the other hand, compared to its crystalline forms, amorphous cabozantinib is believed to show a higher solubility when applied to a patient.

The inventors of the present application have surprisingly found that a composition comprising amorphous solid dispersion of cabozantinib or its pharmaceutically acceptable salt thereof, comprising at least one pharmaceutically acceptable carrier and at least one plasticizer, can increase the solubility of cabozantinib in gastrointestinal tract, and can ameliorate the problem of precipitation or crystallization, thereby increasing the absorption of cabozantinib in vivo and enhance the bioavailability thereof.

In an embodiment, the inventive composition can alter the absorption behavior of cabozantinib in vivo, increasing $C_{max}$ and AUC in fasted state.

In an embodiment, the inventive pharmaceutical composition as described herein, wherein said composition upon oral administration in fasted state exhibits bioequivalence to a commercially available reference drug product (such as CABOMETYX®), in the fasted state, and wherein said bioequivalence is established by at least one of: (i) a confidence interval for mean $AUC_{0-t}$ between about 70% and about 143%; (ii) a confidence interval for mean $AUC_{0-infinity}$ between about 70% and about 143%; (iii) a confidence interval for mean $C_{max}$ between about 70% and about 143% or combinations thereof. Preferably, bioequivalence is established by at least one parameter that is selected from (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125% or combination thereof.

Another embodiment relates to pharmaceutical compositions comprising amorphous solid dispersions of cabozantinib for oral administration, which solid dispersion comprises at least one pharmaceutically acceptable carrier and at least one organic acid, having a fasted state bioavailability that exceeds commercially available product.

Pharmaceutical Compositions Comprising Solid Dispersions of Cabozantinib

The solid dispersion may be used for filling any one of the unit dosage forms described herein (e.g., a capsule) or for tableting. The solid dispersion can optionally be further processed before filling or tableting. Exemplary further processing includes spheronizing, pelletizing, milling, injection molding, sieving, and/or calendaring the solid dispersion.

Amorphous solid dispersions of cabozantinib of the present application can be optionally subjected to a particle size reduction procedure before or after the completion of drying of the product to produce desired particle sizes and distributions. Milling or micronization can be performed to achieve the desired particle sizes or distributions. Equipment that may be used for particle size reduction include, without limitation thereto, ball mills, roller mills, hammer mills, and jet mills.

The amorphous solid dispersion of cabozantinib may be combined with pharmaceutically acceptable excipients to manufacture inventive pharmaceutical compositions. The one or more pharmaceutically acceptable excipients are selected from carrier, pore-forming agents, diluents, binders, disintegrants, lubricants, glidants, surfactants, plasticizers, stabilizing agents, coating agents, antioxidants or combinations thereof.

In an embodiment, pharmaceutical compositions comprising amorphous solid dispersion of cabozantinib and pharmaceutically acceptable excipients are prepared by using, but not limited, to wet granulation, dry granulation, and direct compression.

In an embodiment, pharmaceutical compositions comprising amorphous solid dispersion of cabozantinib or pharmaceutically acceptable salts thereof and pharmaceutically acceptable excipients are prepared by using direct compression, which process comprises mixing amorphous solid dispersion of cabozantinib and pharmaceutically acceptable excipients, and the resultant mixture is either compressed to tablet or filled in hard gelatin capsules.

In an embodiment, pharmaceutical compositions comprising amorphous solid dispersion of cabozantinib and pharmaceutically acceptable excipients are prepared by using dry granulation, wherein dry granulation is carried out by either direct compaction or roller compaction or both.

In an embodiment, pharmaceutical compositions comprising amorphous solid dispersion of cabozantinib and pharmaceutically acceptable excipients are prepared by using direct compaction dry granulation, which process comprises compressing mixture of amorphous solid dispersion of cabozantinib and intragranular material into slug, compressed slugs are milled and passed through mess screen manually or automatically which results in granules. The resulting granules were mixed with extra-granular material. This final mixture is either compressed to tablet or filled in hard gelatin capsules.

In an embodiment, pharmaceutical compositions comprising amorphous solid dispersion of cabozantinib and pharmaceutically acceptable excipients are prepared by wet granulation, which process comprises: (a) mixing amorphous solid dispersion of cabozantinib and pharmaceutically acceptable excipients (b) adding sufficient solvent, wherein the solvent is selected form water, isopropanol, ethanol, to the mixture obtained from step (a) under shear to generate granules; (c) milling or grinding the granules followed by sieving of said granules; optionally mixing with other excipients. This final mixture is either compressed to tablet or filled in hard gelatin capsules.

In particular, the dosage form suitable for oral administration to a patient is a tablet comprises, consists of or consists essentially of: (a) an amorphous solid dispersion of cabozantinib or a pharmaceutically acceptable salt thereof, (b) at least one intra-granular excipient, (c) at least one extra-granular excipient, and (d) optionally, a coating. Intra-granular excipient can be selected from the group containing hydroxypropyl methyl cellulose acetate succinate, polyvinyl pyrrolidine and vinyl acetate (PVP/VA) copolymer, hydroxypropyl methylcellulose phthalate (HPMCP), hydroxypropyl methylcellulose (HPMC), polyethylene glycol (PEG), hydroxypropyl cellulose (HPC), carboxymethyl cellulose (CMC), polyvinyl pyrrolidine (PVP), and mixtures thereof. Extra-granular excipient can be selected from the group containing microcrystalline cellulose, croscarmellose sodium, polyvinyl pyrrolidine (PVP), lactose, colloidal silicon dioxide, magnesium stearate, and mixtures thereof. In an embodiment, the weight of extra-granular excipient is preferably not less than 40% w/w of total composition. In an embodiment, the pharmaceutical composition comprises (a) amorphous solid dispersion of cabozantinib and (b) extra-granular excipients, wherein the weight ratio of the amorphous solid dispersion of cabozantinib to the extra-granular excipient(s) is preferably from about 1:0.3 to about 1:5, more preferably about 1:1.

The pharmaceutical composition of the present invention is preferably a granulate/particulate material. The granules/particles may be filled into a capsule or compressed into a tablet. The tablet may optionally be coated with an additional enteric polymer or an immediate-release coating.

Moreover, the extrudates/granules of the present invention may be formulated into any suitable dosage form, including but not limited to oral suspensions, gels, tablets, capsules, immediate release formulations, delayed release formulations, controlled release formulations, extended-release formulations, pulsatile release formulations, and mixed immediate and controlled release formulations.

Other pharmaceutically acceptable excipients may include, but are not limited to, diluents, binders, disintegrating agents, surfactants, plasticizers, lubricants, glidants, chelating agents, coating agents and the like or mixtures thereof as extra-granular agents.

Suitable diluents include microcrystalline cellulose, calcium carbonate, calcium phosphate-dibasic, calcium phosphate-tribasic, calcium sulfate, cellulose powdered, dextrates, dextrins, dextrose excipients, fructose, kaolin, lactitol, lactose, mannitol, sorbitol, starch, starch pregelatinized, sucrose, sugar compressible, sugar confectioners and the like.

In an embodiment, diluent is included either in intra-granular portion or extra-granular portion or both. The diluent concentration ranges from about 10% to about 60% w/w of total composition. The diluent concentration in the intra-granular portion ranges from about 10% to about 60% w/w of total composition, preferably about 25% to about 35%.

Suitable binders include methyl cellulose, hydroxypropyl cellulose, hydroxypropyl methylcellulose, polyvinyl pyrrolidone, microcrystalline cellulose, gelatin, gum arabic, ethyl cellulose, polyvinyl alcohol, Polyvinylpyrrolidone/vinyl acetate, Pullulan®, pregelatinized starch, agar, tragacanth, sodium alginate, propylene glycol and the like. The concentration of binder ranges from about 1% to about 20% w/w of total composition, preferably about 10% to about 15% w/w.

Suitable pore-forming agents for use in the present invention, but are not limited to, hydrophilic compounds such as silicon dioxide, PVP, HPMC, HPC, lactose, mannitol, PEG, sodium chloride, polysorbate, polyvinyl acetate, gelatin, potassium chloride, sodium laurel sulfate, polyoxyl 40 hydrogenated castor oil, sucrose, sodium chloride, potassium chloride, dextrose, mannitol, glycofurol, transcutol and combinations thereof. The pore-forming agents may be present in an amount ranging from about 0% to about 20% w/w of total composition. The pore-forming agent present in a molar ratio of pore-forming agent to cabozantinib from about 1:1 to about 10:1.

The pore-forming agent forms diffusion pores in the composition, thereby increasing the rate and extent of release of the drug from dosage form. In this respect, a particularly useful pore-forming agent is hydroxypropyl cellulose.

Suitable coating agent may be selected from among hydroxypropylmethylcellulose, hydroxypropylcellulose, methylcellulose, ethylcellulose, hydroxyethylcellulose, cellulose acetate phthalate, sodium ethyl cellulose sulfate, carboxymethyl cellulose, polyvinylpyrrolidone, Pullulan® and an acrylic polymer such as methacrylic acid/methacrylic acid ester copolymers such as methacrylic acid/methylmethacrylate copolymers, etc., and a polyvinyl alcohol. A film-coat composition may comprise a film-forming polymer, water and/or an alcohol as a vehicle, and optionally one or more adjuvants such as are known in the film-coating art. The inventors of the present application have surprisingly found that a composition comprising amorphous solid dispersion of cabozantinib with a film coating contains moisture content less than about 5% w/w in final composition when stored at 25° C. and 60% RH, which prevents the absorption of moisture by amorphous cabozantinib.

Suitable disintegrating agents include croscarmellose sodium, low substituted hydroxypropyl cellulose (L-HPC), sodium starch glycollate, carboxymethyl cellulose, calcium carboxymethyl cellulose, sodium carboxymethyl cellulose, starch, crystalline cellulose, hydroxypropyl starch, pregelatinized starch, and the like and mixtures thereof. The concentration of disintegrating agent ranges from about 1% to about 10% w/w of total composition.

Suitable lubricants/glidants include colloidal silicon dioxide (Aerosil®), stearic acid, magnesium stearate, calcium stearate, talc, hydrogenated castor oil, sucrose esters of fatty acid, microcrystalline wax, yellow beeswax, white beeswax, and the like and mixtures thereof. The concentration of lubricant/glidant ranges from about 0.5% to about 5% w/w of total composition.

Suitable surfactants include both non-ionic and ionic (cationic, anionic and zwitterionic) surfactants suitable for use in pharmaceutical dosage forms. These include polyethoxylated fatty acids and its derivatives, for example, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; ionic surfactants, for example, sodium caproate, sodium glycocholate, soy lecithin, sodium stearyl fumarate, propylene glycol alginate, octyl sulfosuccinate disodium, and palmitoyl carnitine; and the like and mixtures thereof. The concentration of surfactant ranges from about 0.5% to about 10% w/w of total composition.

Suitable colouring agent include dyes and pigments such as iron oxide red or yellow, titanium dioxide, talc. The concentration of colouring agent ranges from about 0.1% to about 1% w/w of total composition.

Suitable chelating agents include, one or more of, but not limited to ethylenediaminetetraacetic acid (EDTA), disodium EDTA and derivatives thereof, citric acid and derivatives thereof, niacinamide and derivatives thereof, and sodium desoxycholate and the like or mixtures thereof. The concentration of chelating agent ranges from about 0.1% to about 1% w/w of total composition.

The pharmaceutical composition, may also optionally be coated, i.e., seal coated and/or enteric coated and/or film coated. Preferably, the pharmaceutical composition may be seal coated and finally film coated or it may be seal coated and further enteric coated. Optionally, pharmaceutical compositions of the invention may be film coated. Preferably, the film coating polymer may be present in an amount from about 2 to 10% w/w.

In yet another embodiment, the invention relates to a kit comprising a) a solid dosage form comprising an effective amount of amorphous solid dispersions of cabozantinib and a pharmaceutically acceptable carrier; and b) instructions for oral administration of the dosage form, which i) do not specify administration with food, or ii) indicate that the dosage form may be administered without regard to food.

Methods of Treatment

The invention provides methods of therapeutically treating proliferative disorders by administering a quantity of: a composition of the invention; composition comprising a composition of the invention; or dosage form comprising a composition of the invention, which administered quantity provides from about 2.5 mg to about 60 mg of cabozantinib per day, either in a single or divided dose. In some embodiments it is preferred to administer daily, in either a single or divided dose an amount of: a composition of the invention or dosage form comprising a composition of the invention which provides from about 2.5 mg to about 60 mg of cabozantinib.

The pharmaceutical composition according to the present invention improves dissolved cabozantinib for absorption of cabozantinib in human body and enhances bioavailability of the drug in comparison to the commercially available product (CABOMETYX®).

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

For administration to animal or human subjects, the pharmaceutical compositions comprise an effective dosage amount of cabozantinib or a pharmaceutically acceptable salt thereof. The composition may be prepared using conventional methods, for example, depending on the subject to be treated, the mode of administration, and the type of treatment desired (e.g., prevention, prophylaxis, or therapy).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

Dissolution Testing

In an embodiment, a stable pharmaceutical composition manufactured in the present application was tested for comparative dissolution by using USP apparatus-II (paddle) in various dissolution media as described below. Preparation of dissolution media required for the studies was prepared as described below:

Dissolution Media-1 (Herein After Referred as DM-1): 0.01 N HCl 0.375% Triton X-100
 Preparation method: Add 8.5 mL of concentrated hydrochloric acid in 10,000 mL of purified water, mix well. Preheat to 37° C.±0.5° C. before starting the dissolution. To this, add 37.5 g of Triton X-100 and sonicate to dissolve completely.

Dissolution Media-2 (Herein After Referred as DM-2): pH 6.8 Phosphate Buffer
 Preparation method: Dissolve 68.0 g of Potassium dihydrogen phosphate monohydrate into 10,000 mL of purified water. Adjust pH with 5N Sodium hydroxide solution to 6.80±0.05. Preheat to 37° C.±0.5° C. before starting the dissolution Dissolution Media-3 (Herein After Referred as DM-3): 0.01 N HCl
 Preparation method: Add 8.5 mL of concentrated hydrochloric acid in 10,000 mL of purified water, mix well. Preheat to 37° C.±0.5° C. before starting the dissolution.

Dissolution Media-4 (Herein After Referred as DM-4): pH Phosphate 6.8 Buffer With 0.25% Triton X-100
 Preparation method: Dissolve 68.0 g of Potassium dihydrogen phosphate monohydrate into 10,000 mL of purified water. Adjust pH with 5N Sodium hydroxide solution to 6.80±0.05. To this, add 25.0 gm of Triton X-100 and sonicate to dissolve completely. Preheat to 37° C.±0.5° C. before starting the dissolution.

Analysis of Samples Withdrawn During In Vitro Dissolution Study

The samples withdrawn from the dissolution study were analyzed for drug content using the following HPLC procedure. The materials and general conditions are listed below:

TABLE 1

| Chromatographic conditions | |
|---|---|
| Chromatographic Mode | Reverse phase Chromatography |
| Column | Kinetex ® PS C18, 100A°, 150 × 4.6 mm, 2.6 μm |
| Wavelength | 324 nm with PDA/UV detector |
| Flow rate | 1.0 mL/min |
| Injection volume | 20 μL |
| Column temperature | 30° C. |
| Sample temperature | 5° C. |
| Run time | 6 minutes |
| Mobile Phase A | Phosphate buffer (20 mM), pH 3.2 |
| Mobile Phase B | Acetonitrile:Methanol:Water in the ratio of 60:30:10 V/V |
| Mode of Elution | Isocratic (Mobile Phase A:Mobile Phase B: 30:70) |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Comparative Example 1

TABLE 2

| Quantitative formula (mg/tablet): Comparative Composition 1 | |
|---|---|
| Ingredients (Quantity~mg/tablet) | |
| Cabozantinib (S)-malate | 76 |
| Avicel ® 102 | 122 |
| Croscarmellose sodium | 17 |
| Lactose Super-Tab 50 | 122 |
| Aerosil ® | 1 |
| Magnesium stearate | 2 |
| Opadry Yellow | 10 |
| Total fill weight | 350 |

Manufacturing Procedure of Composition 1

Cabozantinib (S)-malate, Avicel® 102, Croscarmellose sodium, Lactose Super-Tab 50 and Aerosil® were co-sifted through 30 mesh sieve and mixed for 10 minutes to obtain mixture. The mixture was passed through a 60 mesh sieve. Magnesium stearate was added to above obtained mixture and mixed for 5 minutes to obtain a blend, which was compressed to tablets. Tablets were coated using Opadry yellow. It was observed that cabozantinib-(S)-malate in compressed tablets was in crystalline form.

Example 2

TABLE 3

| Quantitative formula for hot-melt extrudes | | | | | | | |
|---|---|---|---|---|---|---|---|
| | Extrude # | | | | | | |
| | 1A | 1B | 2A | 2B | 2C | 3A | 3B |
| Ingredients (Quantity~mg/batch) | | | | | | | |
| Cabozantinib (S)-malate | 76 | 76 | 76 | 76 | 76 | 76 | 76 |
| HPMC-AS-LMP | 152 | 152 | 228 | 228 | 228 | — | — |
| HPMC-AS-MMP | — | — | — | — | — | 228 | 228 |
| Total weight | 228 | 228 | 304 | 304 | 304 | 304 | 304 |
| Hot-melt extrusion parameters | | | | | | | |
| Temperature (° C.) | 160 | 170 | 150 | 160 | 160 | 150 | 160 |
| Screw speed (RPM) | 250 | 250 | 300 | 300 | 200 | 300 | 200 |
| Feeder (RPM) | — | — | 38 | 50 | 40 | 50 | 40 |

Manufacturing Procedure of Extrude-1A, 1B, 2A, 2B, 2C, 3A and 3B

Cabozantinib (S)-malate with a carrier (HPMC-AS-LMP or HPMC-AS-MMP) was co-sifted through 30 mesh sieve twice and mixed for 10 minutes to obtain a blend. The blend was added to a hopper of a hot-melt extruder at respective temperature in the above table, and the melted extrudes were collected from discharge point. Extrudes were milled using cyclone mill and passed through a 60 mesh sieve.

TABLE 4

| Cabozantinib compositions (60 mg) set forth in below table | | | | |
|---|---|---|---|---|
| | Composition # | | | |
| | 2 | 3 | 4 | 5 |
| Ingredients (Quantity~mg/tablet) | | | | |
| Extrude-1A | 228 | — | — | — |

TABLE 4-continued

Cabozantinib compositions (60 mg) set forth in below table

| Ingredients (Quantity~mg/tablet) | Composition # 2 | Composition # 3 | Composition # 4 | Composition # 5 |
|---|---|---|---|---|
| Extrude-2A | — | 304 | — | — |
| Extrude-2C | — | — | 304 | — |
| Extrude-3A | — | — | — | 304 |
| Cabozantinib:Carrier ratio | 1:2 | 1:3 | 1:3 | 1:3 |
| Microcrystalline cellulose | 55 | 75 | 75 | 75 |
| Croscarmellose sodium | 16 | 20 | 20 | 20 |
| Polyvinyl pyrrolidone K-30 | 15 | 18 | 18 | 18 |
| Lactose | 95 | 125 | 125 | 125 |
| Colloidal silicon dioxide | 2 | 3 | 3 | 3 |
| Magnesium stearate | 4 | 6 | 6 | 6 |
| Coating (Opadry ® Yellow) | — | — | 14 | 14 |
| Total weight | 415 | 551 | 565 | 565 |

Manufacturing Procedure of Compositions 2, 3, 4 and 5

Milled extrudes, microcrystalline cellulose, croscarmellose sodium, polyvinyl pyrrolidone K-30, lactose, colloidal silicon dioxide were passed through a 30 mesh sieve twice and mixed for 10 minutes to obtain a mixture. The mixture was passed through a 60 mesh sieve, magnesium stearate was added and mixed for 5 minutes to obtain a blend. The blend was compressed to obtain tablets. The composition 4 and 5 were further film coated using Opadry® Yellow.

It was observed that cabozantinib (S)-malate was present in amorphous form in compositions 2, 3, 4 and 5.

TABLE 5

Related substances data of milled extrudes (Initial)

| Impurity | Extrude 2B | Extrude 3A | Composition 4 | Composition 5 |
|---|---|---|---|---|
| Hydroxy Impurity | 0.418 | 0.402 | 0.377 | 0.344 |
| Single Unknown Impurity | 1.34 | 1.14 | 1.16 | 1.37 |
| Total Impurity | 2.60 | 2.35 | 2.44 | 2.60 |

Example 3

TABLE 6

Quantitative formula for hot-melt extrudes (gm/batch)

| Ingredients (Quantity~gm/batch) | Extrude # 4A | 4BA | 4BB | 4BC | 4BD | 5 |
|---|---|---|---|---|---|---|
| Cabozantinib (S)-malate | 76 | 76 | 76 | 76 | 76 | 76 |
| Kollidon ® VA64 | 152 | 152 | 152 | 152 | 152 | 228 |
| Total weight | 228 | 228 | 228 | 228 | 228 | 304 |
| Hot-melt extrusion parameters | | | | | | |
| Temperature (° C.) | 160 | 130 | 140 | 145 | 145 | 160 |
| Screw speed (RPM) | 150 | 100 | 100 | 120 | 250 | 200 |
| Feeder (RPM) | 40 | 25 | 25 | 25 | 25 | 50 |

TABLE 7

Related Substance data of Initial milled extrudes

| Impurity | 4AA | 4AB | 4AC | 4AD | 5 |
|---|---|---|---|---|---|
| Hydroxy Impurity | 0.076 | 0.13 | 0.16 | 0.14 | 0.141 |
| Single Unknown Impurity | 0.40 | 0.79 | 0.99 | 0.81 | 0.72 |
| Total Impurity | 0.64 | 1.14 | 1.42 | 1.20 | 1.01 |

Example 4

TABLE 8

Quantitative formula for hot-melt extrudes (gm/batch)

| Ingredients (Quantity~gm/batch) | Extrude # 6A | 6B | 7 |
|---|---|---|---|
| Cabozantinib (S)-malate | 76 | 76 | 76 |
| HPMC-AS-LMP | 266 | 266 | — |
| Kollidon ® VA64 | — | — | 136.8 |
| Kolliphor ® 407 | 38 | 38 | 15.2 |
| Total weight | 380 | 380 | 228 |
| Hot-melt extrusion parameters | | | |
| Temperature (° C.) | 150 | 150 | 130 |
| Screw speed (RPM) | 150 | 300 | 150 |
| Feeder (RPM) | 25 | 25 | 50 |

TABLE 9

Related substances data of milled extrudes (Initial)

| Impurity | 6A | 6B | 7 |
|---|---|---|---|
| Hydroxy Impurity | 0.35 | 0.52 | 0.04 |
| Single Unknown Impurity | 0.71 | 1.08 | 0.22 |
| Total Impurity | 1.71 | 2.55 | 0.51 |

Example 5

TABLE 10

Quantitative formula for hot-melt extrudes (gm/batch)

| Ingredients (Quantity~gm/batch) | Extrude # 8 | 9 |
|---|---|---|
| Cabozantinib (S)-malate | 76.0 | 76 |
| HPMC-AS-LMP | 245.0 | — |
| Kollidon ® VA64 | — | 136.8 |
| PEG-8000 | 57.0 | 13.6 |
| Propyl Gallate | 2.0 | 0.7 |
| Total | 380.0 | 227.1 |
| Hot-melt extrusion parameters | | |
| Temperature (° C.) | 145 | 130 |
| Screw speed (RPM) | 100 | 150 |
| Feeder (RPM) | 50 | 50 |

TABLE 11

Related substances data of milled extrudes (Initial)

| Impurity | Extrude # 8 | Extrude # 9 |
|---|---|---|
| Lab Codes | F073 | F089 |
| Hydroxy Impurity | 0.18 | 0.05 |
| Single Unknown Impurity | 0.18 | 0.22 |
| Total Impurity | 0.57 | 0.41 |

Example 6

TABLE 12

Quantitative formula for hot-melt extrudes (gm/batch)

| | Extrude # 10A | 10B | 10C | 11 | 12 |
|---|---|---|---|---|---|
| Ingredients (Quantity~gm/batch) | | | | | |
| Cabozantinib (S)-malate | 76.0 | 76.0 | 76.0 | 76.0 | 76 |
| HPMC-AS-LMP | 228 | 228 | 228 | 150 | 119 |
| Kollidon ® VA64 | 76 | 76 | 76 | 114 | 114 |
| PEG 8000 | — | — | — | 20 | 51 |
| Poloxamer 407 | — | — | — | 20 | — |
| Tartaric Acid | — | — | — | — | 20 |
| Total | 380.0 | 380.0 | 380.0 | 380.0 | 380.0 |
| Hot-melt extrusion parameters | | | | | |
| Temperature (° C.) | 140 | 130 | 140 | 130 | 140 |
| Screw speed (RPM) | 250 | 350 | 350 | 150 | 150 |
| Feeder (RPM) | 25 | 25 | 25 | 50 | 50 |

TABLE 13

Related substances data of milled extrudes (Initial)

| | Extrude # 10A | 10B | 10C | 11 | 12 |
|---|---|---|---|---|---|
| Impurities (% w/w) | | | | | |
| Hydroxy Impurity | 0.19 | 0.28 | 0.35 | 0.06 | 0.10 |
| Single Unknown Impurity | 0.57 | 1.03 | 1.21 | 0.24 | 0.16 |
| Total Impurity | 1.07 | 1.92 | 2.27 | 0.46 | 0.53 |

Example 7

TABLE 14

Quantitative formula for hot-melt extrudes

| | Extrude # 13A | 13B | 13C | 14A | 14B | 14C | 14D | 15 |
|---|---|---|---|---|---|---|---|---|
| Ingredients (Quantity~gm/batch) | | | | | | | | |
| Cabozantinib (S)-malate | 76 | 76 | 76 | 76 | 76 | 76 | 76 | 76 |
| HPMC-AS-LMP | 102.6 | 102.6 | 102.6 | 150 | 150 | 150 | 150 | 150 |
| Kollidon ® VA64 | 100.6 | 100.6 | 100.6 | 114 | 114 | 114 | 114 | 114 |
| PEG 8000 | 22.8 | 22.8 | 22.8 | 38 | 38 | 38 | 38 | 38 |
| Propyl Gallate | 2 | 2 | 2 | 2 | 2 | 2 | 2 | 2 |
| Total | 304 | 304 | 304 | 380 | 380 | 380 | 380 | 380 |
| HME Process Parameters | | | | | | | | |
| Temperature (° C.) | 130 | 130 | 130 | 130 | 130 | 125 | 120 | 130 |
| Screw RPM | 250 | 250 | 100 | 100 | 150 | 150 | 150 | 125 |
| Feeder RPM | 25 | 50 | 50 | 25 | 50 | 50 | 50 | 6 g/minute |

TABLE 15

Related substances data of milled extrudes (Initial)

| | Extrude # 13A | 13B | 13C | 14A | 14B | 14C | 14D | 15 |
|---|---|---|---|---|---|---|---|---|
| Impurities (% w/w) | | | | | | | | |
| Hydroxy Impurity | 0.16 | 0.11 | 0.09 | 0.10 | 0.06 | 0.05 | 0.04 | 0.06 |
| Single Unknown Impurity | 0.43 | 0.33 | 0.24 | 0.24 | 0.15 | 0.11 | 0.09 | 0.11 |
| Total Impurity | 0.83 | 0.66 | 0.51 | 0.51 | 0.33 | 0.28 | 0.25 | 0.25 |

TABLE 16

Composition of Cabozantinib tablets 60 mg for tablets trial

| | Composition # 6 | 7 |
|---|---|---|
| Ingredients (Quantity~mg/tablet) | | |
| Extrude-14 | 380 | — |
| Extrude-15 | — | 380 |
| Avicel ® PH102 | 271 | 271 |
| Croscarmellose Sodium | 35 | 35 |
| Aerosil ® 200 | 10.5 | 10.5 |
| Magnesium Stearate | 3.5 | 3.5 |
| Total weight (mg) | 700 | 700 |

Manufacturing Procedure of Compositions 6 and 7

Milled extrudes, microcrystalline cellulose, croscarmellose sodium and colloidal silicon dioxide were passed through 40 mesh sieve and mixed for 5 minutes to obtain a mixture. Magnesium stearate was passed through 60 mesh sieve and mixed for 2 minutes to obtain a blend. The blend was compressed to obtain tablets.

Example 8

TABLE 17

Quantitative formula for hot-melt extrudes

| | Extrude # 16A | 16B | 16C | 17 | 18A | 18B |
|---|---|---|---|---|---|---|
| Ingredients (Quantity~gm/batch) | | | | | | |

TABLE 17-continued

Quantitative formula for hot-melt extrudes

| | Extrude # | | | | | |
|---|---|---|---|---|---|---|
| | 16A | 16B | 16C | 17 | 18A | 18B |
| Cabozantinib (S)-malate | 76 | 76 | 76 | 76 | 76 | 76 |
| HPMC-AS-LMP | 148.0 | 148.0 | 148.0 | 148 | 150 | 150 |
| Kollidon ® VA64 | 114.0 | 114.0 | 114.0 | 112 | 114 | 114 |
| PEG 8000 | 38.0 | 38.0 | 38.0 | 38 | 38 | 38 |
| Propyl Gallate | — | — | — | 2 | 2 | 2 |
| Butylated Hydroxy anisole | 4.0 | 4.0 | 4.0 | 4 | — | — |
| Total weight | 380 | 380 | 380 | 380 | 380 | 380 |
| HME Process Parameters | | | | | | |
| Temperature (° C.) | 130 | 130 | 130 | 130 | 130 | 110 |
| Screw RPM | 250 | 250 | 100 | 100 | 150 | 150 |
| Feeder RPM | 25 | 50 | 50 | 50 | 50 | 50 |

TABLE 18

Related substances data of milled extrudes (Initial)

| | Extrude # | | | | | |
|---|---|---|---|---|---|---|
| | 16A | 16B | 16C | 17 | 18A | 18D |
| | Impurities (% w/w) | | | | | |
| Hydroxy Impurity | 0.09 | 0.05 | 0.03 | 0.03 | 0.10 | 0.03 |
| Single Unknown Impurity | 0.33 | 0.19 | 0.12 | 0.1 | 0.24 | 0.08 |
| Total Impurity | 0.66 | 0.44 | 0.28 | 0.24 | 0.51 | 0.22 |

Example 9

TABLE 19

Quantitative formula for hot-melt extrudes (gm/batch)

| | Extrude # | | | | | |
|---|---|---|---|---|---|---|
| | 19 | 20 | 21 | 22 | 23 | 24 |
| Ingredients (Quantity~gm/batch) | | | | | | |
| Cabozantinib (S)-malate | 76 | 76 | 76 | 76 | 76 | 76 |
| HPMC-AS-LMP | 150.0 | 150 | 150 | 173.35 | 187.50 | 187.50 |
| Kollidon ® VA64 | 61.20 | 26.4 | 114 | 80 | 79 | — |
| Plasdone ® S630 Ultra | — | — | — | — | — | 79 |
| Klucel ® EXF | 52.80 | 87 | 58.85 | 80 | 66 | 66 |
| PEG 8000 | 38.0 | 38 | 38 | 47.50 | 47.50 | 47.50 |
| Propyl Gallate | 2.0 | 2 | — | — | — | — |
| Butylated Hydroxy anisole | — | — | — | — | — | — |
| Total weight | 380 | 379.40 | 436.85 | 456.85 | 456 | 456 |
| HME Process Parameters | | | | | | |
| Temperature (° C.) | 130 | 130 | 130 | 130 | 130 | 130 |
| Screw RPM | 150 | 125 | 125 | 125 | 125 | 125 |
| Feeder RPM | 1.5 | 6.0 | 6 | 5.92 | 5.97 | 6 |

TABLE 20

Related substances data of milled extrudes (Initial)

| | Extrude # | | | | | |
|---|---|---|---|---|---|---|
| | 19 | 20 | 21 | 22 | 23 | 24 |
| | Impurities (% w/w) | | | | | |
| Hydroxy Impurity | 0.07 | 0.09 | 0.04 | 0.04 | 0.04 | 0.04 |
| Single Unknown Impurity | 0.18 | 0.22 | 0.17 | 0.15 | 0.13 | 0.15 |
| Total Impurity | 0.38 | 0.52 | 0.37 | 0.33 | 0.31 | 0.31 |

Example 10

TABLE 21

Quantitative formula for hot-melt extrudes

| | Extrude # | | | | | | |
|---|---|---|---|---|---|---|---|
| | 25 | 26 | 27 | 28 | 29 | 30 | 31 |
| Ingredients (Quantity~gm/batch) | | | | | | | |

TABLE 21-continued

Quantitative formula for hot-melt extrudes

| | Extrude # | | | | | | |
|---|---|---|---|---|---|---|---|
| | 25 | 26 | 27 | 28 | 29 | 30 | 31 |
| Cabozantinib (S)-malate | 76 | 76 | 76 | 76 | 76 | 76 | 76 |
| HPMC-AS-LMP | 150 | 150 | 150 | 150 | 154.8 | 168.88 | 176.6 |
| Kollidon ® VA64 | 114 | 87 | 114 | 114 | 118.8 | 50 | 50 |
| Klucel ® EXF | — | 26.4 | — | — | — | 66 | 66 |
| PEG-8000 | 38 | — | 57 | 76 | 30.4 | 19.12 | 11.4 |
| PEG-3350 | — | 2 | — | — | — | — | — |
| Propyl Gallate | 2 | 2 | — | — | — | — | — |
| Total weight | 380 | 380 | 397 | 416 | 380 | 380 | 380 |
| HME Process Parameters | | | | | | | |
| Temperature (° C.) | 130 | 130 | 130 | 130 | 130 | 130 | 130 |
| Screw RPM | 125 | 150 | 150 | 150 | 125 | 125 | 125 |
| Feeder (g/min) | 6 | 1.5 | 1.5 | 1.5 | 5.9 | 6.0 | 6.0 |
| PXRD | Amorphous | Amorphous | Crystalline | Crystalline | Amorphous | Amorphous | Crystalline |

Example 11

Effect of Coating Material on the Stability of the Composition

TABLE 22

Composition of Cabozantinib tablets 60 mg for HME trials

| | Composition # | | |
|---|---|---|---|
| | 8 | 9 | 10 |
| Ingredients (Quantity~mg/batch) | | | |
| Extrude-15 | 380 | 253.33 | 253.33 |
| Stage: Pre-Lubrication and Lubrication | | | |
| Microcrystalline Cellulose | 271 | 180.68 | 180.68 |
| Croscarmellose Sodium | 35 | 23.33 | 23.33 |
| Colloidal Silicon Dioxide | 10.50 | 7 | 7 |
| Magnesium Stearate | 3.50 | 2.33 | 2.33 |
| Core tablet weight | 700 | 466.67 | 466.67 |
| Coating (w/w of total composition) | 2.5% | 4% | 4% |
| Opadry ® (HPMC) | 17.50 | — | — |
| Opadry ® (PVA) AMB | — | 18.67 | — |
| Opadry ® (HPMC) + Pullulan ® | — | — | 18.67 |
| Total weight of coated tablet | 717.50 | 485.34 | 485.34 |
| Temperature (° C.) | 130 | 130 | 130 |
| Screw RPM | 125 | 125 | 125 |
| Feeder (g/min) | 6 | 6 | 6 |

Manufacturing Procedure of Compositions 8, 9 and 10

Milled extrudes, microcrystalline cellulose, croscarmellose sodium and colloidal silicon dioxide were passed through 40 mesh sieve and mixed for 5 minutes to obtain a mixture. Magnesium stearate was passed through 60 mesh sieve and mixed for 3 minutes to obtain a blend. The blend was compressed to obtain tablets, which were coated with coating material as mentioned in Table 22.

Example 12

Effect of Desiccants on the Stability of Compositions

TABLE 23

Composition of Cabozantinib tablets 60 mg

| | Composition # | |
|---|---|---|
| | 11 | 12 |
| Ingredients (Quantity~mg/batch) | | |
| Extrude-14 (A, B, C, D) | 380 | — |
| Extrude-15 | — | 380 |
| Stage: Pre-Lubrication and Lubrication | | |
| Microcrystalline Cellulose | 271 | 271 |
| Croscarmellose Sodium | 35 | 35 |
| Colloidal Silicon Dioxide | 10.50 | 10.50 |
| Magnesium Stearate | 3.50 | 3.50 |
| Core Tablet Total weight | 700 | 700 |
| Stage: Coating (2.5% w/w of total composition) | | |
| Opadry (HPMC) | 17.50 | 17.50 |
| Coated Tablet Total | 717.50 | 717.50 |
| Packaging Material | | |
| Bottle | 60CC HDPE | |
| Storage condition | Condition-1 | Stored separately at two different conditions (i.e., Condition-2 & Condition-3) |

Condition-1 = No desiccant
Condition-2 = 4 Nos. Molecular Sieve + 1g Cotton
Condition-3 = 4 Nos. Silica Gel + 1 g Cotton Manufacturing Procedure of Compositions 11 and 12

Milled extrudes, microcrystalline cellulose, croscarmellose sodium and colloidal silicon dioxide were passed through 40 mesh sieve and mixed for 5 minutes to obtain a mixture. Magnesium stearate was passed through 60 mesh sieve and mixed for 3 minutes to obtain a blend. The blend was compressed to obtain tablets, which were coated with coating material as mentioned in Table 23. Final coated tablets were stored at different conditions as mentioned above.

TABLE 24

Related substances data of compositions 9, 10, 11 and 12

| Compositions (stored at different conditions) | Impurities (% w/w) | Stability Condition | | | | | |
|---|---|---|---|---|---|---|---|
| | | 40° C./75% RH | | | | 25° C./60% RH | |
| | | Initial | 1 M | 3 M | 6 M | 3 M | 6 M |
| Composition 9 (Condition-2) | Hydroxy Impurity | 0.06 | 0.06 | 0.08 | — | 0.04 | — |
| | Single Maximum Unknown Impurity | 0.14 | 0.3 | 0.57 | — | 0.13 | — |
| | Total Impurity | 0.35 | 0.5 | 0.83 | — | 0.26 | — |
| | PXRD | A | A | A | A | A | A |
| Composition 10 (Condition-2) | Hydroxy Impurity | 0.06 | 0.07 | 0.08 | — | 0.06 | — |
| | Single Maximum Unknown Impurity | 0.14 | 0.31 | 0.59 | — | 0.21 | — |
| | Total Impurity | 0.35 | 0.54 | 0.85 | — | 0.41 | — |
| | PXRD | A | A | — | — | — | — |
| Composition 11 (Condition-1) | Hydroxy Impurity | 0.1 | 0.08 | 0.13 | 0.43 | 0.07 | 0.07 |
| | Single Maximum Unknown Impurity | 0.25 | 0.35 | 0.72 | 1.22 | 0.24 | 0.31 |
| | Total Impurity | 0.52 | 0.6 | 1.11 | 2.39 | 0.48 | 0.59 |
| | PXRD | A* | — | C* | C | A | A |
| | Water content (%) | 1.99 | — | 4.83 | — | | |
| Composition 12 (Condition-2) | Hydroxy Impurity | 0.02 | 0.06 | 0.07 | 0.07 | 0.07 | 0.06 |
| | Single Maximum Unknown Impurity | 0.11 | 0.25 | 0.52 | 0.81 | 0.20 | 0.23 |
| | Total Impurity | 0.25 | 0.47 | 0.72 | 1 | 0.43 | 0.37 |
| | PXRD | A | A | A | A | A | A |
| | Water content (%) | 3.22 | — | 4 | — | — | — |
| Composition 12 (Condition-3) | Hydroxy Impurity | 0.02 | 0.07 | 0.09 | 0.1 | 0.06 | 0.06 |
| | Single Maximum Unknown Impurity | 0.11 | 0.28 | 0.62 | 0.99 | 0.22 | 0.25 |
| | Total Impurity | 0.25 | 0.51 | 0.89 | 1.28 | 0.44 | 0.41 |
| | PXRD | | | Not performed | | | |

*A = Amorphous;
*C = Crystalline

Example 13

Effect of Extra-Granular Material on the Cabozantinib Drug Release From

TABLE 25

Composition of Cabozantinib tablets 60 mg

| | Composition # | | | |
|---|---|---|---|---|
| | 13 | 14 | 15 | 16 |
| Ingredients (Quantity~mg/batch) | | | | |
| Extrude-23 | 456 | 456 | 456 | 456 |
| Stage: Pre-Lubrication and Lubrication | | | | |
| Microcrystalline Cellulose | 374.50 | 449.5 | 193.84 | 286.84 |
| Croscarmellose Sodium | 45 | 45 | 32.5 | 37 |
| Colloidal Silicon Dioxide | 20 | 20 | 14.36 | 16.41 |
| Magnesium Stearate | 4.5 | 4.5 | 3.3 | 3.75 |
| Core Tablet Total weight | 900 | 975 | 700 | 800 |
| Stage: Coating (4% w/w of total composition) | | | | |
| Opadry ® (PVA) AMB | 36 | 39 | 28 | 32 |
| Coated Tablet Total | 936 | 1014 | 728 | 832 |

Note:
76 mg of Cabozantinib S-Malate equivalent to 60 mg of Cabozantinib.

Manufacturing Procedure of Composition 13, 14, 15 and 16

Milled extrudes, microcrystalline cellulose, croscarmellose sodium and colloidal silicon dioxide were passed through 40 mesh sieve and mixed for 5 minutes to obtain a mixture. Magnesium stearate was passed through 60 mesh sieve and mixed for 3 minutes to obtain a blend. The blend was compressed to obtain tablets, which were coated with coating material as mentioned in Table 25.

TABLE 26

Composition of Cabozantinib tablets 60 mg for tablets trial

| | Composition # | | | |
|---|---|---|---|---|
| | 17 | 18 | 19 | 20 |
| Ingredients (Quantity~mg/batch) | | | | |
| Extrude-21 | 436.85 | — | — | — |
| Extrude-22 | — | 456.85 | — | — |
| Extrude-23 | — | — | 456 | — |

TABLE 26-continued

Composition of Cabozantinib tablets 60 mg for tablets trial

| | Composition # | | | |
|---|---|---|---|---|
| | 17 | 18 | 19 | 20 |
| Extrude-24 | — | — | — | 456 |
| Stage: Pre-Lubrication and Lubrication | | | | |
| Microcrystalline Cellulose | 443.65 | 448.65 | 449.5 | 449.5 |
| Croscarmellose Sodium | 45 | 45 | 45 | 45 |
| Colloidal Silicon Dioxide | 20 | 20 | 20 | 20 |
| Magnesium Stearate | 4.5 | 4.5 | 4.5 | 4.5 |
| Core Tablet Total weight | 950 | 975 | 975 | 975 |

Example 14

Dissolution Profiles of Comparative Composition-1

When tested by using USP apparatus II (paddle); volume (as mentioned in Table 27) of initial dissolution media for 30 minutes and followed by change-over dissolution media for 60 minutes at 37±0.5° C. and stirred at 75 RPM, the dissolution profiles of Composition-1 were provided in following Table 27. Samples of 10 mL were withdrawn at 10, 15, 20, 30, 45, 60 and 90 minutes from dissolution media. 10 mL dissolution media was added after each sample withdrawal. Withdrawn samples were filtered and analyzed using HPLC system with UV spectrophotometer at a wavelength 324 nm.

TABLE 27

| Time points (minutes) | Comparative Composition-1 | | | | | | | |
|---|---|---|---|---|---|---|---|---|
| | Initial dissolution media (mL) | | | | | | | |
| | DM-1 900 mL | DM-2 900 mL | DM-1 500 mL | DM-2 900 mL | DM-1 500 mL | DM-3 500 ml | DM-3 500 mL | DM-3 500 mL |
| | Drug release (%) | | | | | | | |
| 10 | 94 | — | — | — | — | — | — | — |
| 15 | 96 | 9 | 95 | 1 | 100 | 51 | 53 | 51 |
| 20 | 97 | — | — | — | — | — | — | — |
| 30 | 98 | 10 | 100 | 1 | 103 | 67 | 72 | 70 |
| | Dissolution media added/changed (mL) | | | | | | | |
| | No change | No change | DM-2 400 mL | No change | DM-2 400 mL | DM-2 400 mL | DM-5 400 mL | DM-4 400 mL |
| | Drug release (%) | | | | | | | |
| 45 | — | 11 | 99 | 1 | 102 | 8 | 74 | 73 |
| 60 | — | 12 | 98 | 1 | 102 | 8 | 73 | 73 |
| 90 | — | — | 98 | — | 102 | 6 | 67 | 72 |
| Infinity | 100 | 12 | 98 | 2 | 102 | 6 | 66 | 72 |

Dissolution Profiles of Extrude-1B

When tested by using USP apparatus II (paddle); volume (as mentioned in Table 28) of initial dissolution media for 20 minutes and followed by change-over dissolution media for 70 minutes at 37±0.5° C. and stirred at 75 RPM, the dissolution profiles of Extrude-1B in following Table 28. Samples of 10 mL were withdrawn at 10, 15, 20, 30, 45, 60 and 90 minutes from dissolution media. 10 mL dissolution media was added after each sample withdrawal. Withdrawn samples were filtered and analyzed using HPLC system with UV spectrophotometer at a wavelength 324 nm.

TABLE 28

| Time points (minutes) | Extrude-1B | | | |
|---|---|---|---|---|
| | Initial dissolution media (mL) | | | |
| | DM-1 900 mL | DM-2 900 ml | DM-1 500 mL | DM-2 900 mL |
| | Drug release (%) | | | |
| 10 | 16 | — | — | — |
| 15 | 20 | 75 | 20 | 1 |
| 20 | 24 | — | — | — |
| | Dissolution media added/changed (mL) | | | |
| | No change | No change | DM-2 400 mL | No change |
| | Drug release (%) | | | |
| 30 | 29 | 76 | 29 | 2 |
| 45 | — | 76 | 77 | 2 |
| 60 | — | 77 | 78 | 2 |
| 90 | — | — | 78 | — |
| Infinity | 32 | 77 | 78 | 3 |

Dissolution Profiles of Compositions 11, 12, 17, 18, 19 and 20

When tested by using USP apparatus II (paddle); volume (as mentioned in Table 29) of initial dissolution media for 30 minutes and followed by change-over dissolution media for 60 minutes at 37±0.5° C. and stirred at 75 RPM, the dissolution profiles of Composition-11, 12, 17, 18, 19 and 20 in following Table 29. Samples of 10 mL were withdrawn at 15, 30, 45, 60 and 90 minutes from dissolution media. 10 mL dissolution media was added after each sample withdrawal. Withdrawn samples were filtered and analyzed using HPLC system with UV spectrophotometer at a wavelength 324 nm.

TABLE 29

| Time points (minutes) | Composition # | | | | | |
|---|---|---|---|---|---|---|
| | 11 | 12 | 17 | 18 | 19 | 20 |
| | Initial dissolution media (mL) | | | | | |

TABLE 29-continued

| Time points | Composition # | | | | | |
|---|---|---|---|---|---|---|
| (minutes) | 11 | 12 | 17 | 18 | 19 | 20 |
| | DM-3 | DM-3 | DM-3 | DM-3 | DM-3 | DM-3 |
| | 500 ml | 500 mL | 500 ml | 500 mL | 500 mL | 500 mL |
| | Drug release (%) | | | | | |
| 15 | 40 | 48 | 61 | 64 | 63 | 59 |
| 30 | 45 | 51 | 69 | 76 | 74 | 71 |
| — | Dissolution media added/changed (mL) | | | | | |
| | DM-2 | DM-2 | DM-2 | DM-2 | DM-2 | DM-2 |
| | 400 mL | 400 mL | 400 mL | 400 mL | 400 mL | 400 mL |
| | Drug release (%) | | | | | |
| 45 | 42 | 46 | 52 | 52 | 57 | 51 |
| 60 | 42 | 48 | 46 | 51 | 56 | 50 |
| 90 | 40 | 44 | 46 | 49 | 54 | 49 |
| Infinity | 36 | 39 | 44 | 46 | 55 | 47 |

Dissolution Profiles of Composition-13, 14, 15 and 16

When tested by using USP apparatus II (paddle); volume (as mentioned in Table 30) of initial dissolution media for 30 minutes and followed by change-over dissolution media for 60 minutes at 37±0.5° C. and stirred at 75 RPM, the dissolution profiles of Composition-13, 14, 15 and 16 in following Table 30. Samples of 10 mL were withdrawn at 5, 10, 15, 20 and 30 minutes from dissolution media. 10 mL dissolution media was added after each sample withdrawal. Withdrawn samples were filtered and analyzed using HPLC system with UV spectrophotometer at a wavelength 324 nm.

TABLE 30

| | Composition # | | | |
|---|---|---|---|---|
| | 13 | 14 | 15 | 16 |
| | Dissolution media (mL) | | | |
| | DM-1 | DM-1 | DM-1 | DM-1 |
| Time points | 900 mL | 900 mL | 900 mL | 900 mL |
| (minutes) | Drug release (%) | | | |
| 5 | 42 | 46 | 18 | 27 |
| 10 | 54 | 61 | 32 | 48 |
| 15 | 61 | 70 | 42 | 58 |
| 20 | 67 | 76 | 49 | 64 |
| 30 | 71 | 83 | 58 | 70 |
| Infinity | 76 | 88 | 67 | 79 |

Dissolution Profiles of Composition-13, 14, 15 and 16

When tested by using USP apparatus II (paddle); volume (as mentioned in Table 31) of initial dissolution media for 30 minutes and followed by change-over dissolution media for 60 minutes at 37±0.5° C. and stirred at 75 RPM, the dissolution profiles of Composition-13, 14, 15 and 16 in following Table 31. Samples of 10 mL were withdrawn at 5, 10, 15, 20 and 30 minutes from dissolution media. 10 mL dissolution media was added after each sample withdrawal. Withdrawn samples were filtered and analyzed using HPLC system with UV spectrophotometer at a wavelength 324 nm.

TABLE 31

| | Composition # | | | |
|---|---|---|---|---|
| | 13 | 14 | 15 | 16 |
| | Dissolution media (mL) | | | |
| | DM-4 | DM-4 | DM-4 | DM-4 |
| Time points | 900 mL | 900 mL | 900 mL | 900 mL |
| (minutes) | Drug release (%) | | | |
| 5 | 61 | 69 | 24 | 33 |
| 10 | 82 | 91 | 47 | 74 |
| 15 | 87 | 95 | 63 | 90 |
| 20 | 89 | 95 | 70 | 94 |
| 30 | 88 | 95 | 75 | 94 |
| 45 | 90 | 95 | 82 | 95 |
| Infinity | 91 | 95 | 88 | 95 |

Example 15

A study was conducted to test the pharmacokinetics and bioavailability of Composition 12 in healthy adult, human volunteers, under fasted state.

This study is open label, balanced, randomized two-treatment, three sequence, three-period, single-dose, three-way crossover oral bioequivalence study of Composition 12 and CABOMETYX® 60 mg tablets conducted in 15 healthy, adult, human volunteers under fasted conditions (n=15).

TABLE 32

| Pharmaco-kinetic Parameter | Composition 12 (Fast) | Cabometyx ® 60 mg tablets (Fast) | Composition 12 (Fast)/ Cabometyx ® 60 mg tablets (Fast) (%) | 90% Confidence interval (CI) |
|---|---|---|---|---|
| Cmax (ng/ml) | 279.183 | 361.490 | 77.23 | (56.00%; 106.52%) |
| AUC0-t (ng · hr/mL) | 27098.159 | 26721.706 | 101.41 | (76.73%; 134.02%) |
| AUC0-inf (ng · hr/mL) | 28764.162 | 28057.807 | 102.52 | (78.76%; 133.44%) |

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

Unless specified otherwise, all the percentages, portions and ratios in the present invention are on weight basis.

Unless otherwise indicated, all numbers expressing quantities of ingredients, properties such as molecular weight, reaction conditions, and so forth used in the present specification and associated claims are to be understood as being modified in all instances by the term "about." The terms "about" and "approximate," when used along with a numerical variable, generally means the value of the variable and all the values of the variable within a measurement or an experimental error (e.g., 95% confidence interval for the mean) or within a specified value (e.g., ±10%) within a broader range.

Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

While compositions and methods are described herein in terms of "comprising" various components or steps, the compositions and methods can also "consist essentially of" or "consist of" the various components and steps.

What is claimed is:

1. A pharmaceutical composition suitable for oral administration
   comprising a therapeutically effective amount of cabozantinib in the form of an amorphous solid dispersion and at least one pharmaceutically acceptable excipient,
   wherein said amorphous solid dispersion consists of
   a) cabozantinib or a pharmaceutically acceptable salt thereof;
   b) a pharmaceutically acceptable carrier;
   c) a pore-forming agent selected from group consisting of hydroxypropyl methyl cellulose (HPMC), hydroxypropyl cellulose (HPC), lactose, mannitol, and mixtures thereof; and
   d) a plasticizer,
   wherein said composition can be administered to a human subject without regard to food.

2. The pharmaceutical composition according to claim 1, wherein the pharmaceutically acceptable salt of cabozantinib is cabozantinib(S)-malate.

3. The pharmaceutical composition of claim 1, wherein the pharmaceutical composition comprises from about 2.5 mg to about 140 mg of the cabozantinib.

4. The pharmaceutical composition according to claim 1, wherein the pharmaceutically acceptable carrier b) in the amorphous solid dispersion comprises hydroxypropyl methyl cellulose acetate succinate (HPMC-AS), polyvinyl pyrrolidine and vinyl acetate (PVP/VA) copolymer, hydroxypropyl methylcellulose phthalate (HPMCP), or mixtures thereof.

5. The pharmaceutical composition according to claim 1, wherein the plasticizer d) in the amorphous solid dispersion is polyethylene glycol (PEG).

6. The pharmaceutical composition according to claim 1, wherein a weight percentage of the plasticizer ranges from 4 to 8% w/w of the total composition.

7. The pharmaceutical composition according to claim 1, wherein a weight percentage of the plasticizer ranges from 4 to 14% w/w of the amorphous solid dispersion.

8. The pharmaceutical composition of claim 1, wherein the at least one pharmaceutically acceptable carrier b) in the amorphous solid dispersion is selected from the group consisting of hydroxypropyl methyl cellulose acetate succinate (HPMC-AS), polyvinyl pyrrolidine and vinyl acetate (PVP/VA) copolymer, hydroxypropyl methylcellulose phthalate (HPMCP), carboxymethyl cellulose (CMC), polyvinyl pyrrolidine (PVP), and mixtures thereof.

9. The pharmaceutical composition of claim 1, wherein the amorphous solid dispersion of cabozantinib has a weight ratio of the cabozantinib to the at least one pharmaceutically acceptable carrier from about 1:1 to about 1:6.

10. The pharmaceutical composition of claim 1, wherein the amorphous solid dispersion of cabozantinib has a weight ratio of the cabozantinib to the at least one pharmaceutically acceptable carrier from about 1:1 to about 1:5.

11. The pharmaceutical composition of claim 1, wherein the amorphous solid dispersion of cabozantinib has a weight ratio of the cabozantinib to the at least one pharmaceutically acceptable carrier from about 1:1 to about 1:4.

12. The pharmaceutical composition according to claim 1, wherein the at least one pharmaceutical acceptable excipient is selected from the group consisting of diluents, binders, disintegrants, lubricants, glidants, surfactants, plasticizers, pore-forming agents, stabilizing agents, antioxidants, coating agents and combinations thereof.

13. The pharmaceutical composition according to claim 1, wherein the pharmaceutical composition is a tablet or a capsule.

14. The pharmaceutical composition according to claim 1, wherein said composition provides about 30% enhanced Cmax and about 30% enhanced $AUC_{0-72hr}$, compared to a drug product corresponding to National Drug Code Number 42388-023 and NDA 208692 having the same therapeutically effective amount of cabozantinib, following oral administration in human subjects under fasting condition.

15. The pharmaceutical composition of claim 1, wherein the amorphous solid dispersion of cabozantinib may be prepared by hot-melt extrusion, spray-drying or co-precipitation.

16. The pharmaceutical composition of claim 3, wherein the pharmaceutical composition comprises from about 40 mg of the cabozantinib.

17. The pharmaceutical composition of claim 3, wherein the pharmaceutical composition comprises from about 25 mg of the cabozantinib.

18. The pharmaceutical composition according to claim 1, wherein the pharmaceutically acceptable carrier b) in the amorphous solid dispersion is an enteric or a non-enteric polymer.

* * * * *